(12) United States Patent
Kahn et al.

(10) Patent No.: US 8,568,969 B2
(45) Date of Patent: Oct. 29, 2013

(54) RBP4 IN INSULIN SENSITIVITY/RESISTANCE, DIABETES, AND OBESITY

(75) Inventors: Barbara B. Kahn, Cambridge, MA (US); Qin Yang, Brookline, MA (US); Tim Graham, Newton Center, MA (US); Odile Peroni, Brookline, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 13/477,790

(22) Filed: May 22, 2012

(65) Prior Publication Data
US 2012/0295950 A1   Nov. 22, 2012

Related U.S. Application Data

(60) Continuation of application No. 12/455,324, filed on Jun. 1, 2009, now Pat. No. 8,231,862, which is a division of application No. 11/009,409, filed on Dec. 10, 2004, now Pat. No. 7,553,631.

(60) Provisional application No. 60/528,919, filed on Dec. 11, 2003.

(51) Int. Cl.
*C12Q 1/00* (2006.01)
*C12Q 1/68* (2006.01)

(52) U.S. Cl.
USPC ............................. 435/4; 435/6.1; 435/6.13

(58) Field of Classification Search
USPC ............................................. 435/4, 6.1, 6.13
See application file for complete search history.

(56) References Cited

U.S. PATENT DOCUMENTS

| | | | |
|---|---|---|---|
| 5,399,757 | A | 3/1995 | Maryanoff |
| 6,117,845 | A | 9/2000 | Clagett-Dame et al. |
| 6,544,790 | B1 | 4/2003 | Sabatini |
| 7,553,631 | B2 | 6/2009 | Kahn et al. |
| 8,231,862 | B2 | 7/2012 | Kahn et al. |
| 2002/0006664 | A1 | 1/2002 | Sabatini |
| 2003/0013093 | A1 | 1/2003 | Attie et al. |
| 2003/0032203 | A1 | 2/2003 | Sabatini et al. |

FOREIGN PATENT DOCUMENTS

| | | |
|---|---|---|
| WO | 0222886 | 3/2002 |
| WO | 2004011618 | 2/2004 |
| WO | 2005059564 | 6/2005 |
| WO | 2006052860 | 5/2006 |
| WO | 2006063128 | 6/2006 |

OTHER PUBLICATIONS

Shepherd, P. R., et al., "Adipose Cell Hyperplasia and Enhanced Glucose Disposal in Transgenic Mice Overexpressing GLUT4 Selectively in Adipose Tissue," J. Biol. Chem. 268(30):2243-2246 (1993).
Shi, H., et al., "Determination of Vitamin A in Dried Human Blood Spots by High-performance Capillary Electrophoresis with Laser-Excited Fluorescence Detection," J. Chromatogr. B 665:89-96 (1995).
Sivaprasadarao, A., et al. "The Interaction of Retinol-Binding Protein with its Plasma-Membrane Receptor," Biochem. J. 255(2):561-569 (1988).
Tanumihardjo, S.A., et al., "Dried Blood Spot Retinol and Retinol-binding Protein Concentrations Using Enzyme Immunoassay as Surrogates of Serum Retinol Concentrations," MOST Technical Report. Arlington, Virginia, pp. 1-17 (2002).
Tozzo, E., et al., "Amelioratin of Insulin Resistance in Streptozotocin Diabetic Mice by Transgenic Overexpression of GLUT4 Driven by an Adipose-Specific Promoter," Endocrinology 138(4):1604-1611 (1997).
Um, S.-J., et al., "Antiproliferative Mechanism of Retinoid Derivatives in Ovarian Cancer Cells," Cancer Lett. 174:127-134 (2001).
UniProtKB/Swiss-Prot entry P02753, (Jul. 1986).
Wang, T.T.Y., et al., "Production of Human Plasma Retinol-binding Protein in *Escherichia coli*," Gene 133(2):291-294 (1993).
Written Opinion of the International Searching Authority from International Application No. PCT/US2004/041383, Dated: May 19, 2005.
Xie, Y., et al., "Recombinant Human Retinol-Binding Protein Refolding, Native Disulfide Formation, and Characterization," Protein Express. Purif. 14:31-37 (1998).
Yang, Q., et al., "Serum Retinol Binding Protein 4 Contributes to Insulin Resistance in Obesity and Type 2 Diabetes," Nature, 436:356-362 (May 2005).
Abahusain, M.A., et al., "Retinol, Alpha-Tocopherol and Carotenoids in Diabetes," Eur. J. Clin. Nutr. 53:630-635 (1999).
Abel, E. D., et al., "Adipose-selective Targeting of the GLUT4 Gene Impairs Insulin Action in Muscle and Liver," Nature 409:729-733 (2001).
Advisory Action dated Oct. 22, 2008 for U.S. Appl. No. 11/009,409.
Basu, T.K., et al., "Serum Vitamin A and Retinol-Binding Protein in Patients with Insulin-dependent Diabetes Mellitus," Am. J. Clin. Nutr. 50:329-331 (1989).
Basu, T.K., et al., "Vitamin A Homeostasis and Diabetes Mellitus," Nutrition 13(9):804-806 (1997).
Basualdo, C. G., et al., "Vitamin A (Retinol) Status of First Nation Adults with Non-Insulin-Dependent Diabetes Mellitus," J. Am. Coll. Nutr. 16(1):39-45 (1997).
Berni, R., et al., "In Vitro Interaction of Fenretinide With Plasma Retinol-Binding Protein and Its Functional Consequences," FEBS Lett., 308(1): 43-45 (1992).
Berni, R., et al., "Retinoids: In Vitro Interaction with Retinol-binding Protein and Influence on Plasma Retinol," FASEB J. 7:1179-1184 (1993).
Blaner, W. S., "Retinol-Binding Protein: The Serum Transport Protein for Vitamin A," Endocr. Rev. 10(3):308-316 (1989).
Carvalho, E., et al., "Overexpression of Glut4 in Fat 'Rescues' Glucose Intolerance in Muscle-Specific Glut4 Knockout Mice," Journal of the American Diabetes Association 51 Supplement (2): (From Diabetes Abstract Book, 2002, A326, Abstract No. 1333-P).

(Continued)

Primary Examiner — Thaian N Ton
(74) Attorney, Agent, or Firm — Hamilton Brook Smith Reynolds, PC

(57) ABSTRACT

Methods for screening molecules that modulate the activity of Retinol Binding Protein 4 (RBP4) and their use in treatment of insulin resistance are described. Also described are methods of diagnosing insulin resistance and related conditions by detecting modulation of RBP4 activity.

14 Claims, 25 Drawing Sheets

(56) References Cited

OTHER PUBLICATIONS

Chambon, P., "A Decade of Molecular Biology of Retinoic Acid Receptors," FASEB J. 10:940-954 (1996).
Christensen, E.I., et al., "Evidence for an Essential Role of Megalin in Transepithelial Transport of Retinol," J. Am. Soc. Nephrol. 10:685-695 (1999).
Communication Pursuant to Article 96(2) EPC from European Patent Application No. 04813676.6, Dated Jun. 21, 2007.
Communication Pursuant to Rules 109 and 110 EPC from European Patent Application No. 04813676.6, Dated: Jul. 26, 2006.
Craft, N.E., "Innovative Approaches to Vitamin A Assessment," American Society for Nutritional Sciences131:1626S-1630S (2001).
de Pee, S., et al., "Biochemical Indicators of Vitamin A Deficiency: Serum Retinol and Serum Retinol Binding Protein," J. Nutr. 132:2895S-2901S (2002).
DesPres, J.-P., et al., "Hyperinsulinemia as an Independent Risk Factor for Ischemic Heart Disease," N. Engl. J. Med., 334(15):952-957 (1996).
Dykxhoorn, D.M., et al., "Killing the Messenger: Short RNAs that Silence Gene Expression," Nature Rev., 4:457-467 (2003).
Fukenstein, B., "Developmental Expression, Tissue Distribution and Hormonal Regulation of Fish (*Sparus aurata*) Serum Retinol-Binding Protein," Comp. Biochem. Physiol. B, 129(2-3), 613-622 (2001).
Gnudi, L., et al., "Adipose-specific Overexpression of GLUT-4 in Transgenic Mice Alters Lipoprotein Lipase Activity," Am. J. Physiol. 270(4):R785-R792 (1996).
Graham, T.E., et al., "Retinol-Binding Protein 4 and Insulin Resistance in Lean, Obese and Diabetic Subjects," N. Engl. J. Med., 354: 2552-2563 (Jun. 2006).
Holven, K.B., et al., "Secretion of N-(-4-hydroxphenyl) Retinamide-Retinol-Binding Protein from Live Parenchymal Cells: Evidence for Reduced Affinity of the Complex for Transthyretin," Int. J. Cancer, 71:654-659 (1997).
International Preliminary Report on Patentability from International Application No. PCT/US2004/041383, Dated: Jun. 22, 2006.
International Search Report from International Application No. PCT/US2004/041383, Dated: May 19, 2005.
Interview Summary dated Aug. 1, 2008 for U.S. Appl. No. 11/009,409.
Jaconi, S., et al., "Characterization of Two Post-translationally Processed Forms of Human Serum Retinol-binding Protein: Altered Ratios in Chronic Renal Failure," J. Lipid Res. 36:1247-1253 (1995).
Jessen, K.A., and Satre, M.A., "Mouse Retinol Binding Protein Gene: Cloning, Expression and Regulation by Retinoic Acid," Mol. Cell. Biochem., 211(1-2): 85-94 (2000).
Kemp, S.F., and Frindik, J.P., "Effect of Metabolic Control on Serum Protein Concentrations in Diabetes," Acta Paediatr. Scand. 80(10):938-943 (1991).
Kiernan, U.A., et al., "Comparative Phenotypic Analyses of Human Plasma and Urinary Retinol Binding Protein Using Mass Spectrometric Immunoassay," Biochem. Biophys. Res. Comm. 297:401-405 (2002).

Kim, Y.-B., et al., "Glucosamine Infusion in Rats Rapidly Impairs Insulin Stimulation of Phosphoinositide 3-Kinase but does not Alter Activation of Akt/Protein Kinase B in Skeletal Muscle," Diabetes 48:310-320 (1999).
Lee, C.-H., et al., "Minireview: Lipid Metabolism, Metabolic Diseases, and Peroxisome Proliferator-Activated Receptors," Endocrinology 144(6):2201-2207 (2003).
Lorenzo, C., et al., "The Metabolic Syndrome as Predictor of Type 2 Diabetes," Diabetes Care 26(11):3153-3159 (2003).
Malpeli, G., et al., "Retinoid Binding to Retinol-binding Protein and the Interference with the Interaction with Transthyretin," Biochimica et Biophysica Acta 1294:48-54 (1996).
Matarese, V., and Lodish, H.F.,"Specific Uptake of Retinol-binding Protein by Variant F9 Cell Lines," J. Biol. Chem., 268(25):18859-18865 (1993).
Meigs, J.B., "The Metabolic Syndrome," BMJ 327:61-62 (2003).
Merritt, R.J., et al., "Consequences of Modified Fasting in Obese Pediatric and Adolescent Patients: Effect of a Carbohydrate-free Diet on Serum Proteins," Am. J. Clin. Nutr. 34:2752-2755 (1981).
Minokoshi, Y., et al., "Tissue-specific Ablation of the GLUT4 Glucose Transporter or the Insulin Receptor Challenges Assumptions about Insulin Action and Glucose Homeostasis," J. Biol. Chem. 278(36):33609-33612 (2003).
Notice of Allowance and Fees dated Mar. 12, 2009 for U.S. Appl. No. 11/009,409.
Notice of Allowance and Fees Due dated Mar. 20, 2012 for U.S. Appl. No. 12/455,324.
Office Action dated Jun. 22, 2011 for U.S. Appl. No. 12/455,324.
Office Action dated Jun. 25, 2008 for U.S. Appl. No. 11/009,409.
Office Action dated Oct. 25, 2007 for U.S. Appl. No. 11/009,409.
Office Action for Japanese Applciation No. 2006-544010, Mail Date: Aug. 3, 2010.
Osei, K., et al., "Is Glycosylated Hemoglobin A1c a Surrogate for Metabolic Syndrome in Nondiabetic, First-Degree Relatives of African-American Patients with Type 2 Diabetes?," J. Clin. Endocrinol. Metab. 88(10):4596-4601 (2003).
Quadro, L., et al., "Impaired Retinal Function and Vitamin A Availability in Mice Lacking Retinol-Binding Protein," EMBO Journal, 18(17): 4633-4644 (1999).
Response to Rule 312 Communication dated Jun. 15, 2012 for U.S. Appl. No. 12/455,324.
Saltiel, A.R., and Olefsky, J.M., "Thiazolidinediones in the Treatment of Insulin Resistance and Type II Diabetes," Diabetes, 45(12): 1661-1669 (1996).
Schaffer, E.M., et al., "N-(4-Hydroxyphenyl)retinamide (Fenretinide) Induces Retinol-Binding Protein Secretion from Liver and Accumulation in the Kidneys in Rats," J. Nutr., 123(9): 1497-1503 (1993).
Sheikh, M.S., et al., "N-(4-hydroxyphenyl)retinamide (4-HPR)-mediated Biological Actions Involve Retinoid Receptor-Independent Pathways in Human Breast Carcinoma," Carcinogenesis 16(10):2477-2486 (1995).
Shen, Q., et al., "Effects of Rexinoids on Glucose Transport and Insulin-mediated Signaling in Skeletal Muscles of Diabetic (db/db) Mice," J. Biol. Chem. 279(19):19721-19731 (2004).

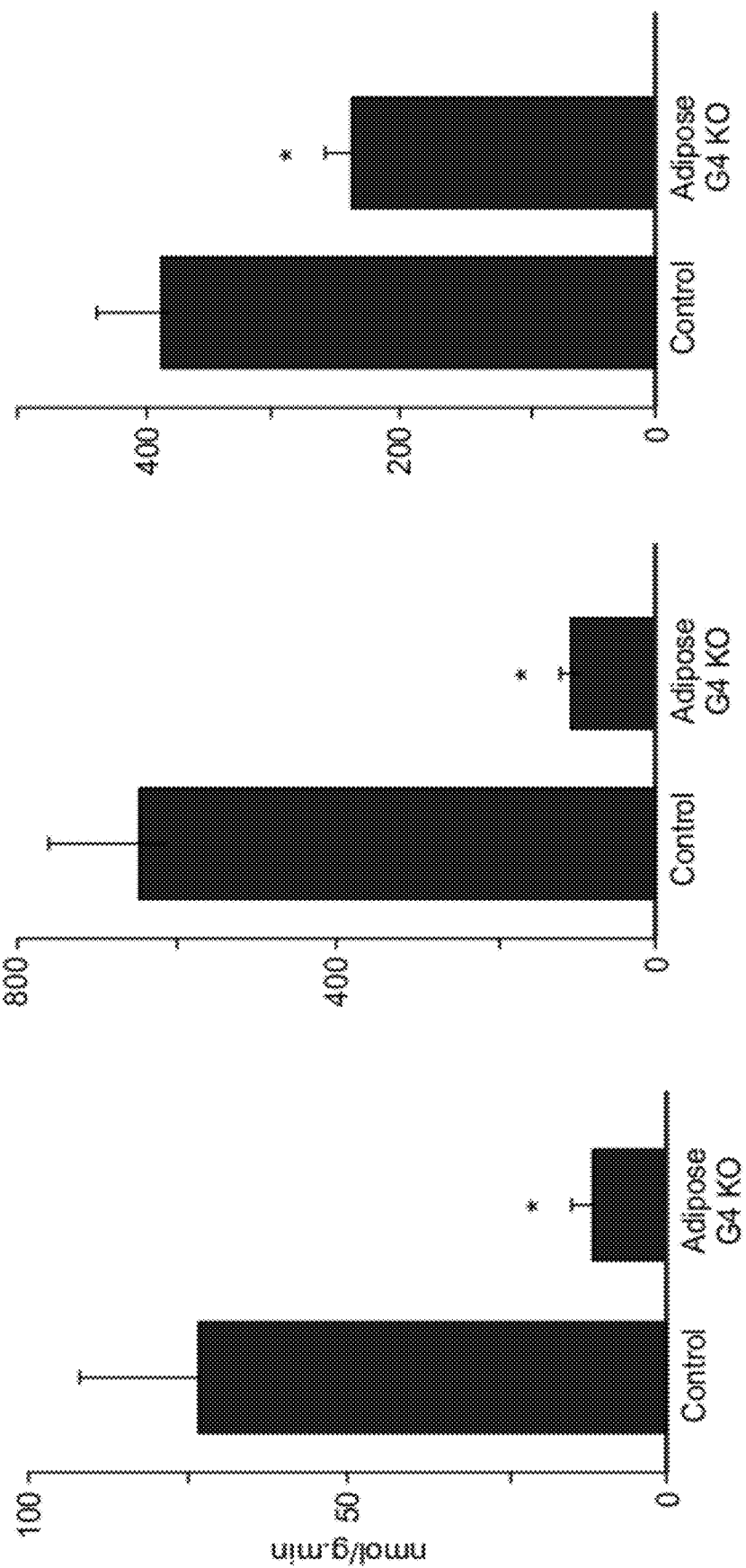

| Parameters | MCK-RBP4 transgenic mice | | | RBP4 knock out mice | | |
|---|---|---|---|---|---|---|
| | WT | Tg | | WT | Het | KO |
| Body Weight (g) | 28.7 ± 1.7 | 28.6 ± 2.2 | | 28.0 ± 2.6 | 28.1 ± 2.1 | 27.1 ± 2.1 |
| Glucose (mg/dl) | 150 ± 24 | 153 ± 13 | | 152 ± 16 | 159 ± 20 | 167 ± 19 |
| Insulin (ng/ml) | 0.64 ± 0.16 | 0.97 ± 0.18* | | 1.19 ± 0.41 | 1.01 ± 0.30 | 0.90 ± 0.28 |
| FFA (mmol/l) | 0.30 ± 0.05 | 0.39 ± 0.1 | | 0.51 ± 0.2 | 0.36 ± 0.08* | 0.37 ± 0.1* |
| Leptin (ng/ml) | 5.7 ± 4.0 | 4.7 ± 1.7 | | 6.3 ± 3.6 | 4.7 ± 2.3 | 5.9 ± 2.6 |
| Adiponectin (μg/ml) | 8.8 ± 2.2 | 8.2 ± 0.9 | | 9.9 ± 1.3 | 9.0 ± 0.9 | 9.1 ± 1.7 |
| Resistin (ng/ml) | 25.4 ± 2.2 | 26.2 ± 3.9 | | 23.9 ± 2.3 | 23.0 ± 3.1 | 21.0 ± 2.6 |

FIG. 21

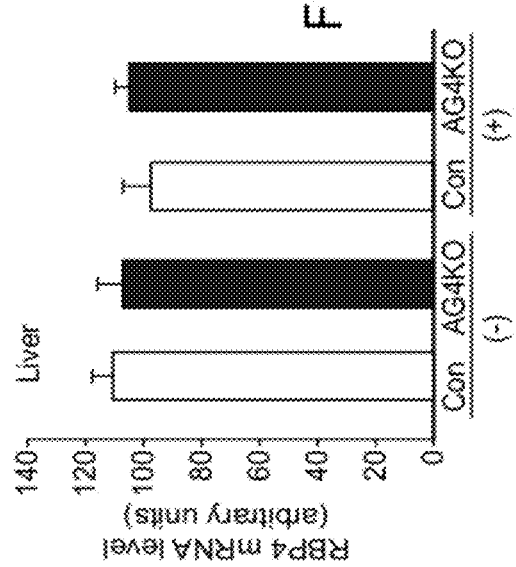
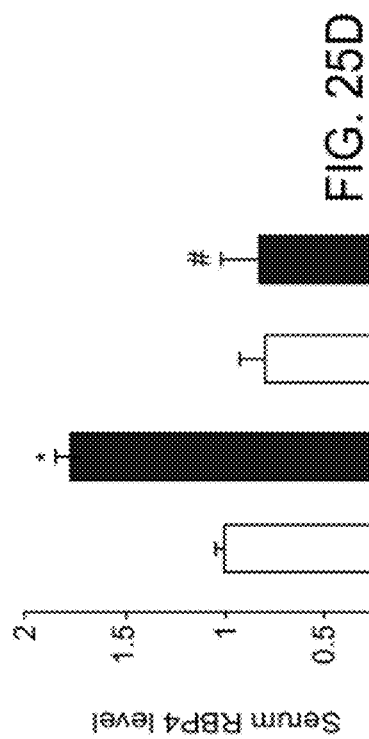
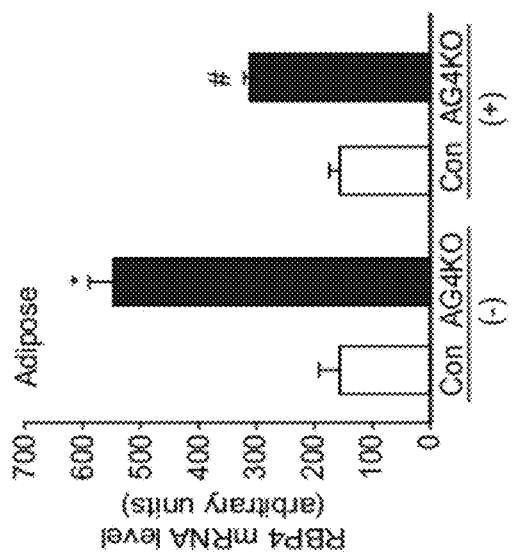
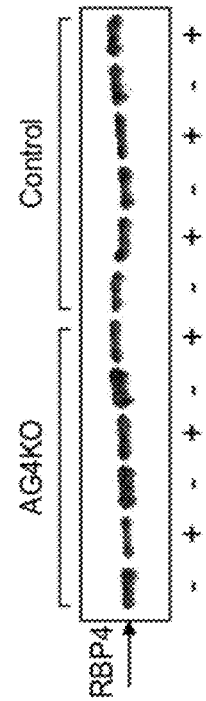
FIG. 25A
FIG. 25B
FIG. 25C
FIG. 25D

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
tctgtggacg agaagggtca t                                              21

<210> SEQ ID NO 2
<211> LENGTH: 21
<212> TYPE: DNA
<213> ORGANISM: Artificial Sequence
<220> FEATURE:
```

```
<223> OTHER INFORMATION: Primer

<400> SEQUENCE: 2
ccagttgctc agaagacgga c                                              21

<210> SEQ ID NO 3
<211> LENGTH: 21
<212> TYPE: DNA
<213> ORGANISM: Artificial Sequence
<220> FEATURE:
<223> OTHER INFORMATION: Probe

<400> SEQUENCE: 3
tgagcgccac agccaaggga c                                              21
```

RBP4 IN INSULIN SENSITIVITY/RESISTANCE, DIABETES, AND OBESITY

RELATED APPLICATIONS

This application is a continuation of U.S. application Ser. No. 12/455,324, filed Jun. 1, 2009, now U.S. Pat. No. 8,231,862, which is a divisional of U.S. application Ser. No. 11/009,409, filed Dec. 10, 2004, now U.S. Pat. No. 7,553,631, which claims the benefit of U.S. Provisional Application No. 60/528,919, filed Dec. 11, 2003. The entire teachings of the above applications are incorporated herein by reference.

GOVERNMENT SUPPORT

The invention was supported, in whole or in part, by a grant RO1DK43051 from the National Institutes of Health. The Government has certain rights in the invention.

BACKGROUND OF THE INVENTION

Insulin resistance in the peripheral tissues such as muscle and fat is associated with increased secretion of insulin by pancreatic $\beta$-cells. The secreted insulin promotes glucose utilization and inhibits production of glucose by the liver. However, the pancreatic $\beta$-cells often cannot sustain the increased production of insulin resulting in the eventual decrease of insulin production and glucose intolerance.

Insulin resistance is characterized, for example, by increased glucose concentration in the blood, increased insulin concentration in the blood, decreased ability to metabolize glucose in response to insulin, or a combination of any of the above. Insulin resistance is thought to predict possible later development of diabetic disease, such as Type 2 Diabetes. However, even in the absence of diabetes, insulin resistance is a major risk factor for cardiovascular disease (Despres, et al., *N. Engl. J. Med* 334:952-957 (1996)). The loss of insulin production in insulin resistance and diabetes results in increased blood glucose or hyperglycemia. Hyperglycemia in turn can contribute to long term illness such as nephropathy, neuropathy, and retinopathy.

Insulin resistance is also associated with abnormalities in glucose and lipid metabolism, obesity, kidney disease, high blood pressure and increased risk for cardiovascular disease. The association of insulin resistance with these other abnormalities is referred to as "Insulin Resistance Syndrome" or "Metabolic Syndrome" or "Syndrome X". In particular, Metabolic Syndrome has been characterized as the co-occurrence of obesity (especially central obesity), dyslipidemia (especially high levels of triglycerides and low levels of high density lipoprotein cholesterol), hyperglycemia and hypertension. People with Metabolic Syndrome are at increased risk for diabetes or cardiovascular disease relative to people without the syndrome (Meigs, J. B., *BMJ*: 327, 61-62, (2003)).

Decreased expression of the insulin responsive glucose transporter, GLUT4, is seen in adipocytes in nearly all insulin resistant states in humans and rodents (Shepherd, P. R. and Cohn, B. B., *N Engl. J. Med.* 341:248-257 (1999)). However, the mechanism by which decreased expression of GLUT4 contributes to systemic insulin resistance has not been clear because adipose tissue contributes very little to total body glucose disposal.

Due to the association of insulin resistance with later development of diabetes and cardiovascular disease, and the prevalence of insulin resistance worldwide, the need exists for additional metabolic or endocrine targets for the development of treatments that alleviate or mitigate diseases associated with insulin resistance. A need also exists for additional detection/diagnostic methods of insulin resistance, Metabolic Syndrome and Type II diabetes to allow for the earliest possible intervention through life-style changes and/or medication.

SUMMARY OF THE INVENTION

The present invention provides important new targets and screening methods for the detection and/or identification of molecules or agents that can be used for the development of treatments that alleviate or mitigate symptoms and diseases associated with insulin resistance, Metabolic Syndrome, and Type 2 diabetes. As shown herein for the first time, elevation of serum of Retinol Binding Protein 4 (RBP4) causes insulin resistance and impaired glucose tolerance, whereas lowering of serum RBP4 improves insulin action and glucose tolerance. The results in several mouse models of insulin resistance are confirmed by human data. Furthermore, treatment of ob/ob mice with a retinamide that disrupts the interaction between RBP4 and transthyretin thereby leading to a lowering of plasma RPB4 levels, and a reduction in long-term morbidity. It appears that RBP4 may be a mechanistic link by which down regulation of GLUT4 expression in adipocytes causes systemic insulin resistance.

As described herein, RBP4 can be used as an early marker for insulin resistance and related conditions such as Metabolic Syndrome, because an increased level of RBP4 is correlated with insulin resistance in humans and mice, even in the absence of, or before the occurrence of, conditions related to insulin resistance such as diabetes and/or obesity. In addition, RBP4 is a novel target to develop treatments that reduce insulin resistance. Furthermore, reduction of RBP4 activity in individuals with insulin resistance is a novel therapy for treatment of insulin resistance and related conditions.

The present invention relates to methods for identifying compounds that modulate RBP4 activity. The methods comprise contacting RBP4 with a test compound and comparing the level of RBP4 activity in the presence of the test compound to the level of RBP4 activity in the absence of the test compound to determine modulation of RBP4 activity, wherein an alteration of RBP4 activity is indicative of a compound that modulates RBP4 activity.

The present invention also relates to methods of identifying compounds that reduce circulating levels of RBP4 in a mammal. Such methods include in vitro and in vivo methods. In one embodiment, the method comprises the steps of administering a test compound to the mammal, obtaining a sample (such as a urine sample or blood sample) from the mammal, and comparing the level of RBP4 in the sample after administration of the test compound to the level of RBP4 in a control sample prior to administration of the test compound, wherein an increase in RBP4 in the urine sample or decrease in the blood sample after administration of the test compound as compared to the control sample is indicative of a compound that reduces in circulating levels of RBP4.

The present invention also relates to methods of reducing insulin resistance in a mammal. The method comprises administering to a mammal a compound that reduces the activity of RBP4.

The present invention also relates to methods of diagnosing insulin resistance or a related condition in a mammal. The methods comprise measuring RBP4 activity in a biological sample obtained from the mammal, wherein an increase in RBP4 activity is indicative of insulin resistance or related condition.

Using RBP4 as a marker for insulin resistance or related conditions is advantageous because it does not require fasting or any special preparation by the patient, RBP4 is a stable compound under routine collection conditions, and RBP4 can be detected in a blood drop from a skin prick, or in urine.

In addition, using RBP4 as a marker for insulin resistance or related conditions may be useful in many at risk populations including obese and non-obese relatives of individuals with Type 2 diabetes patients with other criteria for the metabolic syndrome such as hypertension and in or hyperlipidemia and polycystic ovarian syndrome. RBP4 levels may also be useful to distinguish between Type 1 and Type 2 diabetes in newly diagnosed patients.

BRIEF DESCRIPTION OF THE DRAWINGS

FIG. 8A shows insulin-stimulated 2-deoxyglucose transport in vivo in white adipose tissue (WAT) from control (left bar) and AG4KO mice (right bar).

FIG. 8B shows insulin-stimulated 2-deoxyglucose transport in vivo in brown adipose tissue (BAT) from control (left bar) and AG4KO mice (right bar).

FIG. 8C shows insulin-stimulated 2-deoxyglucose transport in vivo in muscle from control (left bar) and AG4KO mice (right bar).

FIG. 21 is a table comparing the indicated parameters of MCK-RBP4 transgenic mice (Tg) with wild-type (WT) and RBP4 knockout mice (KO) with wild-type (WT) and heterozygous (Het) mice.

serum was obtained at the indicated times and hRBP4 was diluted to the indicated concentrations as the standard.

Figure 22B:
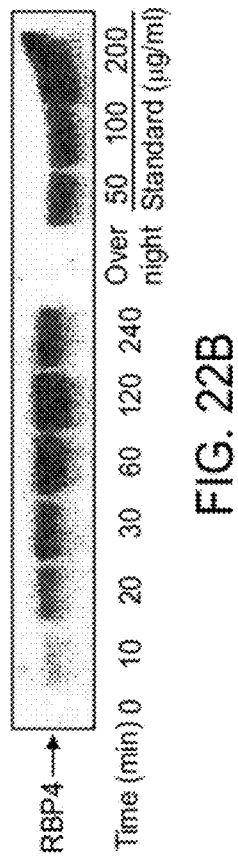
FIG. 22B is a Western blot of serum from an FVB mouse injected i.p. with 0.5 mg recombinant human RBP4 (hRBP4)
Figure 22D:
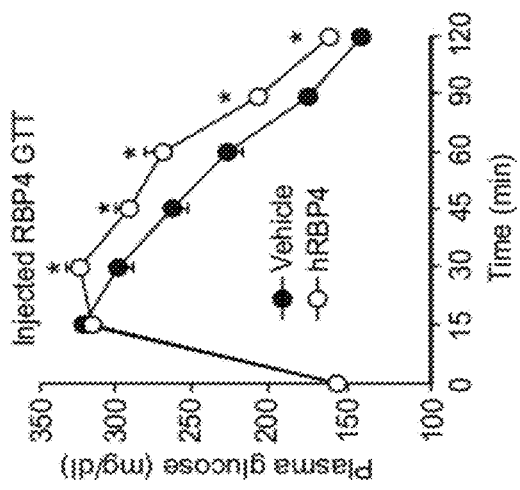
FIG. 22A shows plasma glucose measured at the indicated times in 12 week old male wild-type (WT) or RBP4 transgenic (Tg) mice (n=7 per genotype) injected i.p. with insulin (0.9 U/kg body weight) 4 hours after the food removal. Data are means±SEM. *P<0.01 vs. (WT).
Figure 22A:
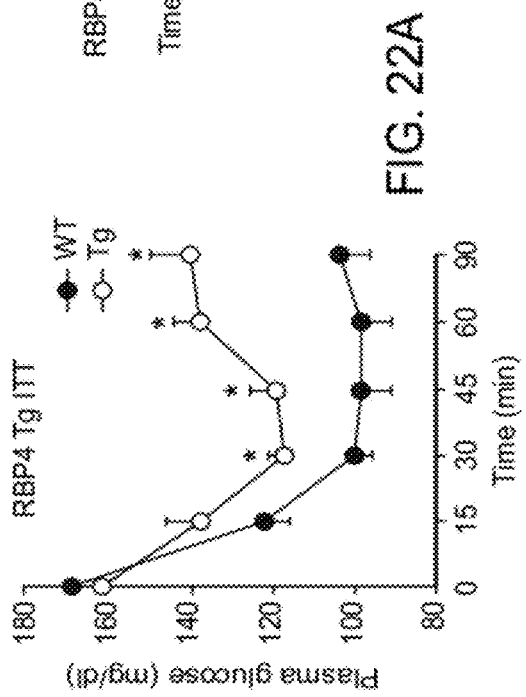
Figure 22C:
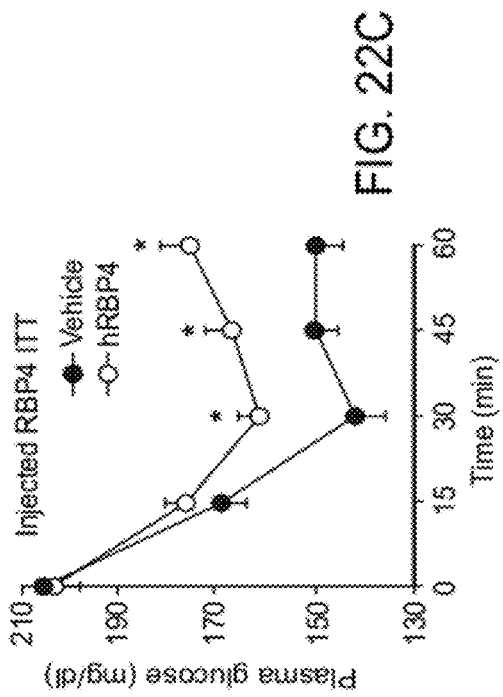

FIG. 22C shows the results of an insulin tolerance test (ITT) in mice injected chronically with purified hRBP4; ITT (0.9 U/kg insulin) was performed after 19 days of injections. n=8 for control mice, n=12 for hRBP4 injected mice. *P<0.01.

FIG. 22D shows the results of a glucose tolerance test (GTT) in mice injected chronically with purified hRBP4; GTT (1 g/kg glucose) was performed after 9 days of injections. n=8 for control mice, n=12 for hRBP4 injected mice. *P<0.01.

Figure 23A:
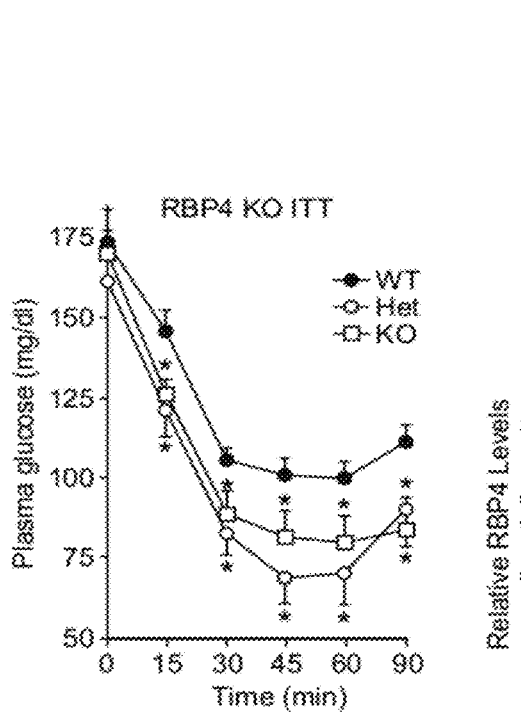

FIG. 23A shows the results of ITT in male RBP4 KO mice at 10 weeks of age; insulin (0.75 U/kg) was injected i.p., n=7-9 per genotype. Data are means±SEM. *P<0.01 vs. WT at each time point.

Figure 23B:
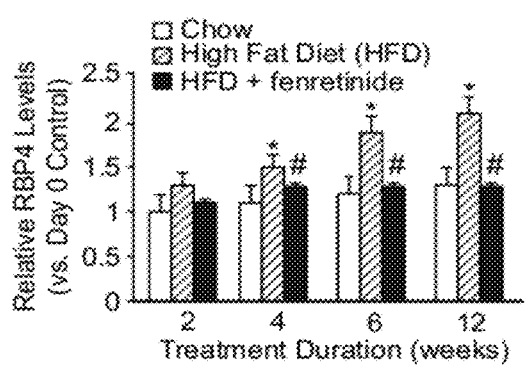

FIG. 23B shows a representative immunoblot of serum RBP4 in mice fed for 6 weeks with chow, high fat diet (HFD) or HFD with 0.04% fenretinide.

Figure 23C:
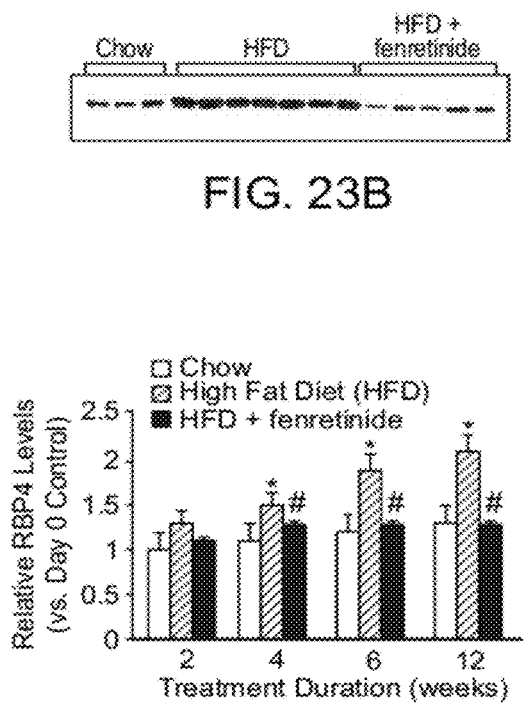

FIG. 23C shows densitometric quantitation of immunoblots of serum RBP4 levels in mice fed with chow, HFD, or HFD with fenretinide for the indicated periods of time; n=8-12 per condition. *P<0.05 vs. chow diet, #P<0.05 vs. HFD.

Figure 23D:
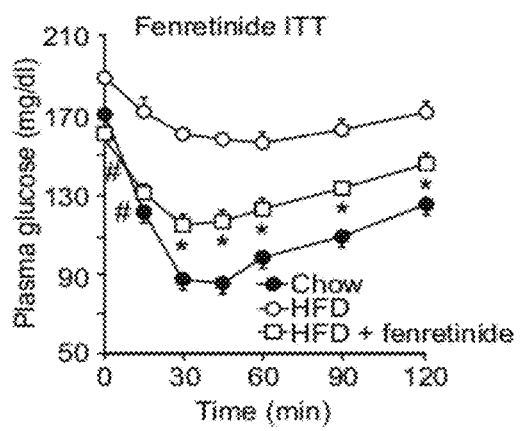

FIG. 23D shows the results of an ITT in mice fed with chow, HFD, or HFD with fenretinide; after 15 weeks of treatment, ITT was performed using 1.1 U/kg insulin. *P<0.05 vs. HFD and chow. #P<0.05 vs. HFD only. n=6-10 mice per condition.

Figure 23E:
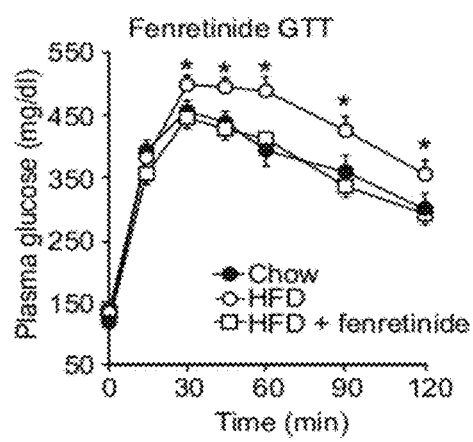

FIG. 23E shows the results of a GTT using 2 g/kg glucose in mice fed with chow, HFD, or HFD with fenretinide for 16 weeks (n=8-12 mice per condition). *P<0.01 vs. chow and HFD with fenretinide and chow groups.

Figure 24A:
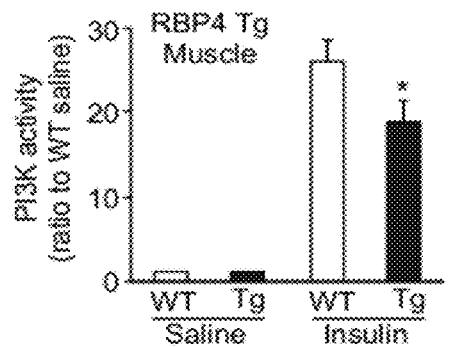
Figure 24B:
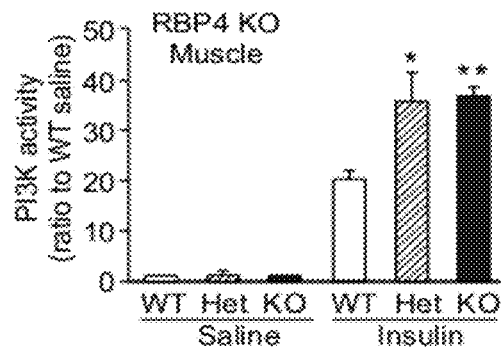

FIGS. 24A and 24B show PI3K activity in muscle of saline- or insulin-injected RBP4 Tg mice (A) and RBP4 KO mice (B) (n=4 for saline, n=6 for insulin). *P<0.05 vs. WT insulin, **P<0.01 vs. WT insulin.

Figure 24C:
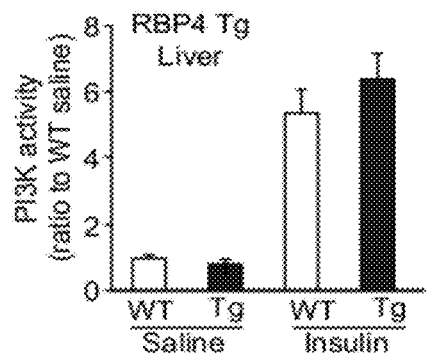
Figure 24D:
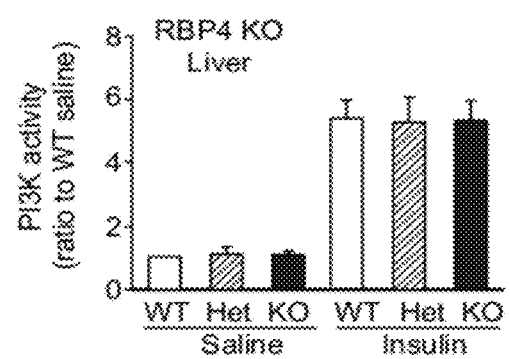

FIGS. 24C and 24D show PI3K activity in liver or saline of insulin-injected RBP4 Tg mice (C) and RBP4 KO mice (D) (n=4 for saline, n=6 for insulin). Mice were 16 week of age. PI3K activity was measured in anti-phosphotyrosine immuniprecipitates.

Figure 24E:
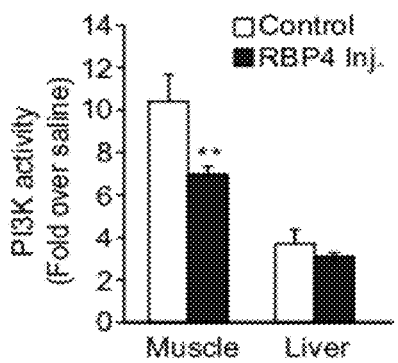

FIG. 24E shows insulin-stimulated PI3K activity in muscle and liver of normal FVB mice injected with i.p. with purified hRBP4 (n=4 for vehicle controlled mice treated with insulin, n=9 for RBP4 injected mice treated with insulin); PI3K activity in saline-injected mice did not differ between groups; data are expressed as fold stimulation by insulin over the basal (saline-injected) level. **P<0.01 vs. vehicle control vs. RBP4-injected mice.

Figure 24F:
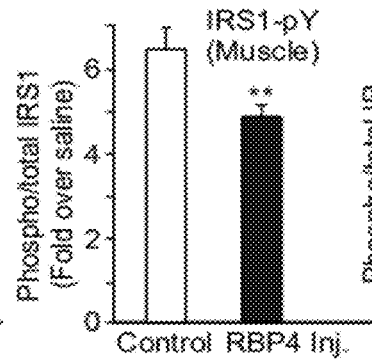

FIG. 24F shows insulin-stimulated tyrosine phosphorylation of Insulin Receptor Substrate-1 (pY612) in muscle of normal FVB mice injected i.p. with purified human RBP4 (n=for vehicle controlled mice treated with insulin, n=9 for RBP4 injected mice treated with insulin); the basal (saline-injected) level of IR phosphorylation and IRS1 phosphorylation did not differ between groups; data were corrected for the total amount of IRS1 or IR protein for each sample and expressed as fold stimulation by insulin over the basal level. **P<0.01 vehicle control vs. RBP4-injected mice.

Figure 24G:
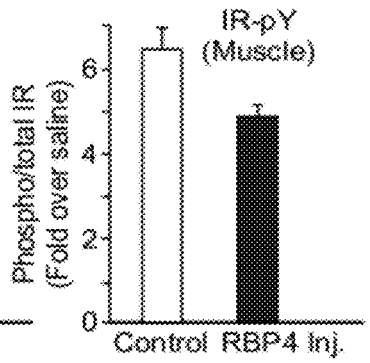

FIG. 24G shows insulin stimulated tyrosine phosphorylation of insulin receptor (pY972) in muscle of normal FVB mice; treatment, sample size, and statistics are as described for FIG. 24E.

FIG. 25A shows the level of mRNA in adipose tissue of AG4KO and control (FVB) mice at 11 weeks of age, treated with TZD (+) or without (−), (n=2-6 per condition).

FIG. 25B shows the level of RBP4 mRNA from the liver of AG4KO or control (FVB) mice treated with or without TZD (n=6 per group).

FIG. 25C shows serum RBP4 levels from AG4KO and control (FVB) mice before (−) and after (+) TZD treatment; mice were 8 weeks of age before treatment and 11 weeks of age after.

FIG. 25D shows the densitometric quantitation of western blots from FIG. 25C where * is P<0.05 versus control (TZD−) and # is P<0.05 versus AG4KO (TZD−).

Figure 26A:
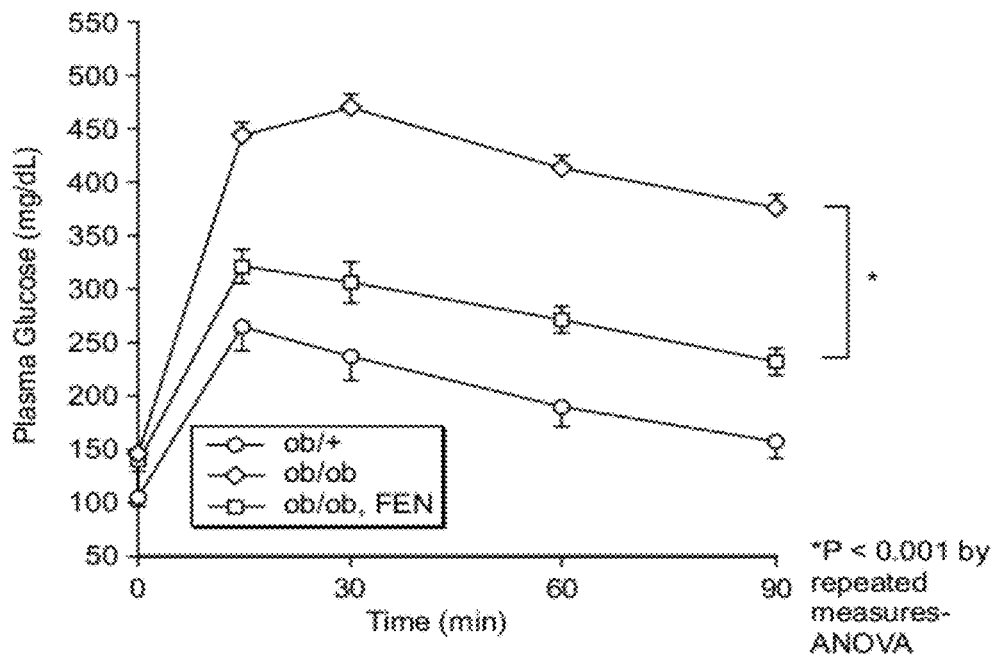

FIG. 26A shows the level of plasma glucose over time in 12 week old mice after IP-GTT (2 mg/g body weight) in mice treated with fenretinide for 8 weeks; open circles=ob/+ mice, closed circles=ob/ob mice; and open squares=ob/ob mice treated with fenretinide.

Figure 26B:
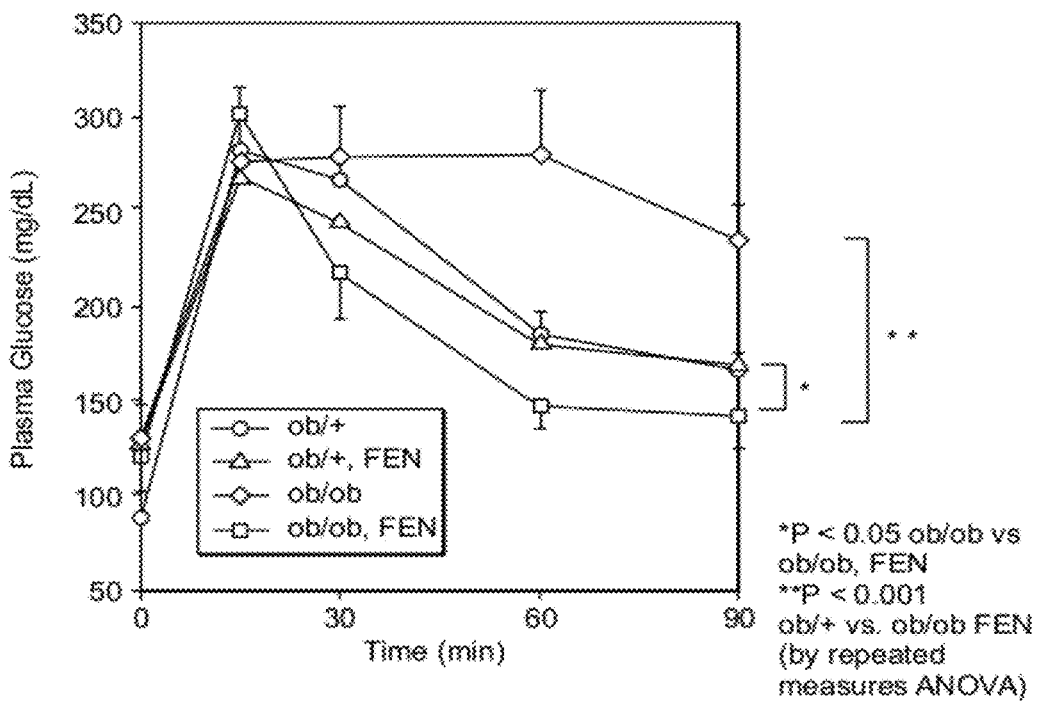

FIG. 26B shows the level of plasma glucose over time in 42 week old mice after IP-GTT (1 mg/g body weight) in mice treated with fenretinide for 8 weeks; closed squares=ob/+ mice, closed circles=ob/+ mice treated with fenretinide, open squares=ob/ob mice; and open circles=ob/ob mice treated with fenretinide.

Figure 26C:
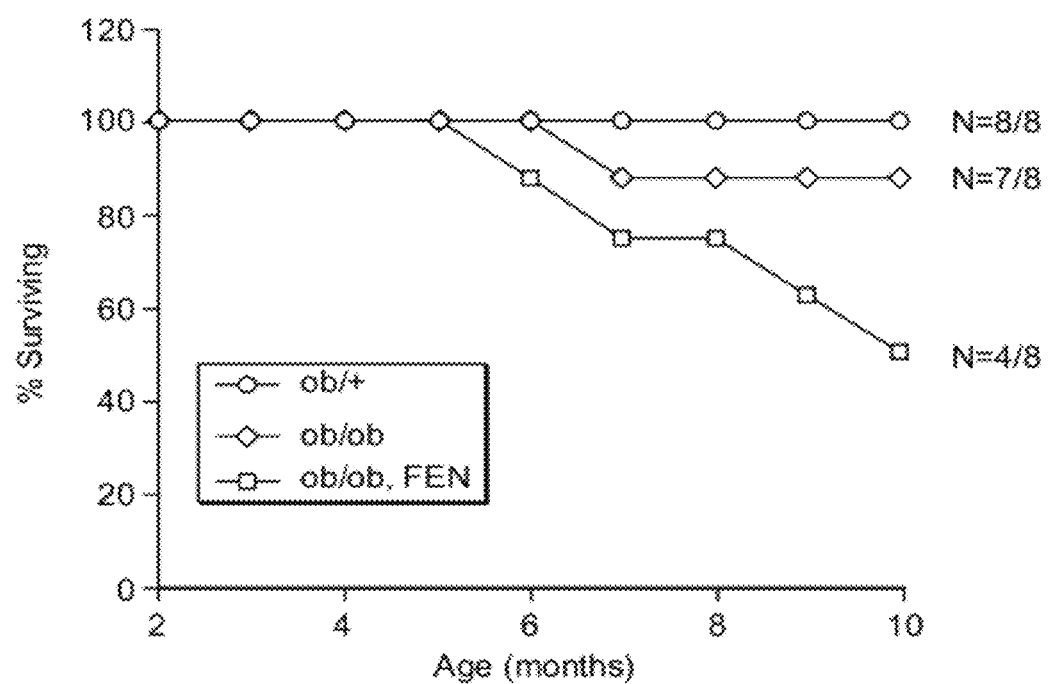

FIG. 26C shows the percent of mice surviving at the indicated times where closed squares=ob/+ mice, closed circles=ob/ob mice treated with fenretinide; and closed squares=ob/ob mice.

DETAILED DESCRIPTION OF THE INVENTION

It is demonstrated herein for the first time that a soluble factor is correlated with insulin resistance and that factor is RBP4. RBP4 is correlated with insulin resistance, even in the absence of diabetes and/or obesity. Therefore, RBP4 is a useful target for screening compounds that reduce insulin resistance, as well as for early diagnosis and treatment of insulin resistance. As described herein, RBP4 is elevated in the serum of mice where the insulin responsive glucose transporter (GLUT4) has been specifically knocked out in adipose tissue (AG4KO mice). AG4KO is a mouse model for insulin resistance.

As demonstrated herein, RBP4 can be used as an early marker for insulin resistance, diabetes such as Type 2 diabetes, and Metabolic Syndrome because it is shown that AG4KO mice have elevated levels of serum RBP4 and are insulin resistant, but are normal in their fat content and adipocyte morphology as well as in their weight (Example IB).

As described in example ID, a soluble factor is responsible for the insulin resistance in AG4KO mice because insulin-stimulated glucose transport in muscle from these mice is impaired in vivo in spite of having preserved expression of GLUT4. Furthermore, GLUT4 activity is normal when the muscle is tested ex vivo. In addition, as described in Example IIA, serum from AG4KO mice inhibits glucose transport in 3T3-L1 adipocytes. Furthermore, RBP4 was identified as being elevated in the serum of AG4KO mice and reduced in the serum of mice that overexpress GLUT4 in adipose tissue as shown in Example IIB.

As demonstrated herein, modification of RBP4 activity is a target for methods of treatment for insulin resistance and for conditions related to insulin resistance. In particular, detection of RBP4 activity can be the basis for screening methods to identify compounds useful for the treatment of insulin resistance and related conditions. As shown in Example IIIC, a thiazolidinene compound that alleviates insulin resistance also reverses the increase in RBP4. In addition, as shown in Example IIID, fenretinide, a compound that disrupts the interaction between RBP4 and transthyretin resulting in increased secretion of RBP4 in the urine, improved insulin sensitivity and normalized glucose tolerance in mice on a high fat diet. As shown in Example IIID, RBP4 knockout mice are more insulin sensitive, yet their body weight is not altered compared to control animals. In addition, other mouse models of insulin resistance have elevated RBP4 levels (Example III). Importantly, fenretinide treatment improves long-term morbidity in ob/ob mice (Example IIIC).

Human data agrees with the mouse model data. As described herein, serum RBP4 levels are elevated in obese and obese/diabetic humans but not in lean/non-diabetic humans (Example IV).

RBP4 may act through retinol-dependent or retinol-independent mechanisms. While not wishing to be bound by theory, increased serum RBP4 levels may influence insulin action in extrahepatic tissues because retinol content depends primarily on the availability of dietary retinol, and RBP4 mediates transport of retinol from the liver to extrahepatic tissues (Blaner, W. S., *Endocr. Rev.* 10:308-316 (1989)). Consistent with this, as demonstrated herein, in both RBP4 overexpressing mice (Tg) and RBP4-treated mice, insulin resistance is associated with impaired insulin-stimulated PI3K activity in muscle but not in liver. Retinol-dependent mechanisms by which RBP4 may influence insulin action include, but are not limited to, increased production of retinoic acid isomers, or altered tissue metabolism of retinoic acid isomers, the active forms of retinol that interact with retinoic acid receptors (RARs) and retinoic acid-X receptors (RXRs) to regulate gene transcription (Chambon, P., *FASEB J.* 10: 940-954 (1996)). Consistent with this, a 20-46% increase in mRNA levels of retinoic acid-dependent genes (retinoic acid receptor-data-2, and cellular retinoic acid binding protein I) was observed in muscle of RBP4 overexpressing mice.

RBP4 may also cause insulin resistance through retinol-independent mechanisms. Evidence suggests that RBP4 binds at high affinity and with high specificity to cell surface receptors that could potentially modulate intercellular signal transduction (Sivaprasadarao, A. and Findlay, J. P., *Bio Chem J.* 255:561-569 (1998); Matarase, V. and Lodish, H. F., *J. Biol. Chem.* 268:18859-18865 (1993)). Megalin-gp320 is the only RBP4 receptor identified to date in peripheral tissues and is a non-specific receptor for macromolecular complexes. (Christensen, E. I., et al. *J. Am. Soc. Nephrol.* 10:685-695(1999)). The megalin-RBP4 interaction is low affinity (Kd 2 µM); a high affinity receptor for RBP4 has not been identified. Further possibilities for retinol-independent actions of RBP4 include transport and delivery of non-retinoid molecules. The possibility that RBP4 may transport other lipophilic molecules besides retinol is confirmed by its ability to bind a wide range of other retinoids in vitro (Bernie, R., et al., *FASEB J.* 7:1179-1184 (1993)). RBP4 could also modulate transthyretin function.

Regardless of the mechanism by which elevated serum RBP4 contributes to insulin resistance, as demonstrated herein for the first time, normalization of serum RBP4 by fenretinide treatment leads to improvements in insulin action and glucose tolerance in insulin resistant obese mice. Furthermore, treatment of ob/ob mice with fenretinide reduces long-term morbidity. While not wishing to be bound by theory, increased excretion of RBP4 is likely a major action by which fenretinide reverses insulin resistance in obese rodents. Fenretinide and its metabolites lack a terminal carboxyl group, an essential feature of active retinoids. Furthermore, fenretinide does not activate RXR isoforms in vitro, indicating that the insulin-sensitizing effects of fenretinide are different from those of selective RXR agonists (i.e., rexinoids) (Sheikh, M. S., et al., *Carcinogenesis* 16:2477-2478 (1995); Um, S. J., et al., *Cancer letters* 174:127-134 (2001); Shen, Q., et al., *J.* *Biol. Chem.* 279:19721-19731 (2004)). While there may be additional mechanisms by which fenretinide improves insulin-glucose homeostasis, as demonstrated herein, RBP4-transthyretin interaction is a novel target for the development of drugs to combat insulin resistance and type 2 diabetes.

Methods for Screening Compounds that Modulate RPB4 Activity

As described herein, the present invention relates to methods for identifying compounds that modulate the activity of RBP4 in vivo, e.g., in a mammal or in vitro, wherein the ability of the compound to modulate RBP4 activity was previously unknown.

Methods of identification include in vitro or in vivo methods. The method of the present invention can be used to identify compounds that decrease RBP4 activity or to identify compounds that increase RBP4 activity.

In one embodiment of identifying compounds that modulate RBP4 activity, a biological sample, comprising a suitable cell, tissue, serum, plasma, or urine is contacted with one or more test compounds and the level of RBP4 activity in the sample in the presence of the test compound is compared with the level of RBP4 activity in the absence of the test compound, wherein a difference in the level of RBP4 activity is indicative of a compound that modulates RBP4 activity.

As described herein, RBP4 activity includes, for example, expression of RBP4 mRNA or protein. RBP4 activity also includes the ability of RBP4 to bind TTR, the ability of RBP4 to bind retinol, the ability of RBP4 to bind cells, stability (e.g. structural or half-life) of RBP4 in tissues or in circulation, the ability of RBP4 to deliver retinol to cells, and the ability of RBP4 to activate cell signaling, for example, activation of nuclear hormone receptors.

In one embodiment, compounds that modulate the activity of RBP4 reduce the level of insulin resistance in a mammal. For example, as demonstrated herein, reduction of the ability of RBP4 to interact with TTR is correlated with a reduction in insulin resistance. Symptoms of insulin resistance include, for example, impaired glucose tolerance, impaired insulin-stimulated glucose transport, impaired insulin signaling, increased levels of serum glucose, and/or increased levels of serum insulin. These indicators of insulin resistance can be measured using standard methods in the art including the methods described herein.

In one embodiment, RBP4 activity is the expression level of RBP4, and the level of expression of RBP4 is detected. RBP4 expression can be measured by detecting the level of RBP4 mRNA in the cells or tissue. Techniques for detecting RNA levels are well known in the art and include reverse transcriptase PCR (RT-PCR), Northern blotting, and RNAse protection assays. In addition, the rate at which RBP4 mRNA is transcribed can be determined using a RBP4 promoter reporter assay or a nuclear run-off assay. See "Current Protocols in Molecular Biology" Vol. 1, Chapter 4, John Wiley & Sons, Inc. (1997). Quantitative real time RT-PCR can be employed to assess RBP4 mRNA stability. See Howe et al., *Clin Chem.* (2003); Bustin S A, *J Mol Endocrinol.* 29(1):23-29 (2002). See also, for example, U.S. Pat. No. 6,544,790, the teachings of which are incorporated by reference. RBP4 expression can also be measured by detecting the level or concentration of RBP4 protein or a biologically active fragment thereof. For example, any method suitable for detecting protein/peptide levels in tissue or cells can be used, such as specific antibody binding (immunological or immunoreactive method, e.g., ELISA, RIA, nephlometry or Western blot) to detect the levels of RBP4, or a biologically active fragment thereof, or a characteristic fragment thereof (i.e., a fragment that may not have all of the biological activity of the intact RBP4 protein, but can be used to specifically identify the biologically active protein).

Suitable cells or tissues for use in the identification assays described herein include adipose, liver, and muscle. Alternatively, for example, methods described herein can compare the level of RBP4 in the blood of an individual prior to and after the administration of a test compound. Blood samples include, for example, whole blood, plasma, or serum. Urine, stool, and other bodily fluids can also be used.

The present invention also relates to methods of screening for compounds that inhibit the binding of RBP4 to cells. For example, the method can determine the binding of RBP4 to adipose cells or muscle cells in the presence and absence of the test compound, wherein decreased binding of RBP4 to the cells in the presence of the test compound indicates that the test compound is effective in reducing binding of RBP4 to the cells.

The activity of RBP4 also encompasses the ability of RBP4 to bind to its blood carrier protein, transthyretin (TTR). Thus, the present invention also includes methods to screen compounds for their ability to reduce the binding of RBP4 to transthyretin, for example, by comparing the amount of RBP4 bound to transthyretin in the presence or absence of the test compound, wherein a reduction in binding of RBP4 to transthyretin is indicative of the ability of the test compound to inhibit or reduce the binding of RBP4 to transthyretin. Such in vitro methods for evaluating RBP4 binding or reduction in binding to TTR are well known to those of skill in the art.

The ability of RBP4 to bind TTR can be measured, for example, by release of RBP4 from immobilized transthryretin (also referred to herein as TTR); release of TTR from immobilized RBP4; inhibition of RBP4-TTR interactions as monitored using standard techniques in the art, for example, by loss of FRET (fluorescent resonance energy transfer) conducted with chromophore-labeled or EP fusion proteins, or by surface plasmon resonance with immobilized RBP4 or TTR.

The present invention also includes methods to screen compounds for their ability to modulate the ability of RBP4 to bind to retinol. Such methods include detecting compounds that reduce the ability of RBP4 to bind retinol as well as compounds that increase the ability of RBP4 to bind retinol and are well known in the art. In vitro binding assays are well known to those of skill in the art and can include, for example, ELISA and RIA.

The assays can also include RBP4 promoter-reporter assays, in vitro mRNA translation and stability assays, RBP4 secretion assays using primary hepatocytes, or half-life studies of RBP4 stability in cell culture conditions (ex-vivo) or in vitro.

The method to identify compounds that modulate RBP4 activity includes methods that measure the ability of RBP4 to deliver retinol to tissues and influence levels of biologically active retinoids in tissues and circulation. In particular, the assays can detect molecules that modulate RBP4 regulation/activation of nuclear hormone receptors; regulate PPARγ signaling; RXR signaling; RAR signaling; LXR signaling and signaling by other nuclear receptors that directly or indirectly interact with RAR or RXR. These assays can also detect molecules that modulate RBP4 regulation of LRAT or CYP26 mRNA expression. The assays described herein include high throughput assays.

Methods of identifying compounds that modulate RBP4 activity also include in vivo methods. For example, the animal models for insulin resistance described herein can be used. In vivo methods of testing RBP4 activity and/or insulin resistance include methods described, for example, in Exemplification. For example, mice having insulin resistance such as AG4KO mice can be treated with or without the test compound and then subjected to glucose tolerance test or insulin tolerance test, wherein improved glucose tolerance or insulin tolerance is indicative of a compound that modulates RBP4 activity. In another embodiment, the level of RBP4 in serum can be compared between the two groups of mice, wherein the reduction in level of RBP4 in the blood is indicative of a compound that modulates RBP4 activity. Furthermore, blood glucose and plasma insulin level can be measured in mice, wherein a lower level of blood glucose and/or a lower plasma insulin level in treated mice compared to nontreated mice is indicative of a compound that modulates RBP4 activity. In another embodiment, wild type mice can be administered a high-fat diet, and treated with the test compound, or not. The levels of RBP4 can be compared between treated and nontreated mice wherein the reduction in the level of RBP4, is indicative of a compound that modulates RBP4 activity. Furthermore, the treated and nontreated mice on a high fat diet can be given the glucose tolerance test or the insulin tolerance test, wherein the reduction in glucose levels in the blood or plasma insulin levels is indicative of a compound that modulates or RBP4 activity and thereby modulates insulin resistance. As used herein, modulation includes both inhibition and increase in activity, where inhibition is any measurable level of reduced activity, and increase is any measurable level of activity.

As described herein, any compound that modulates RBP4 activity can also be useful for therapeutic treatment to alleviate conditions related to insulin resistance.

Compounds that interfere with the binding of RBP4 and TTR, resulting in increased renal clearance of circulating RBP4, are candidates for treatment of insulin resistance and related conditions in a mammal. The candidate molecule can be subsequently tested in assays to confirm the ability of the molecule to reduce insulin resistance.

Antibodies, either polyclonal, monoclonal, or antibody fragments that specifically bind to either RBP4 or TTR can also be used to interfere with RBP4/TTR binding. The production of such specific antibodies is well-known to those of skill in the art.

Examples of the molecules that interfere with the binding of RBP4 and transthyretin include molecules that structurally mimic the natural ligand of RBP4. In one embodiment, the molecule is a retinamide or retinyl ester or a retinamide/retinyl ester mimic. The retinamide or retinyl ester disrupts the RBP4-TTR complex in circulation, resulting in urinary wasting of RBP4 and a reduction in circulating RBP4 levels. The molecules such as the retinamides or retinyl esters described herein can, optionally, have a higher binding affinity to RBP4 than that of retinol, retinal or retinoic acid. In one embodiment, the retinamide or retinyl ester possesses one or more bulky side-chains or other prosthetic groups. In another embodiment, the retinamide or retinyl ester disrupts the RBP4-TTR complex and does not act as a downstream agonist in retinol dependent signaling.

All-trans isomeric form of retinamides and retinyl esters are characterized by Structural Formula (1) shown below:

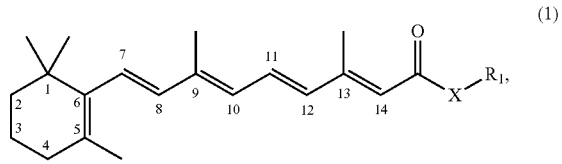

(1)

where X is —NR'— or —O—; and $R_1$ is a substituted or unsubstituted aliphatic or aryl group, or a substituted or unsubstituted non-aromatic heterocyclic group; and R' is hydrogen or a substituted or unsubstituted aliphatic or aryl group, or a substituted or unsubstituted non-aromatic heterocyclic group. It is noted that other isomers of the molecules characterized by Structural Formula (1), for example, 7-cis, 9-cis, 11-cis, 13-cis, or any combination thereof, can also be used in the invention. 9-cis and 13-cis isomers are exemplified in Structural Formulas (2) and (3), where X and $R_1$ are as defined above:

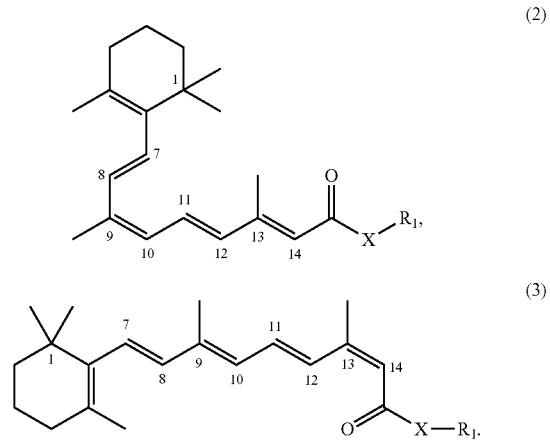

Typically, $R_1$ is a substituted or unsubstituted aryl or lower alkyl group. Preferably, when X is —NR'—, $R_1$ is a substituted aryl group, such as 4-hydroxy phenyl, 3-hydroxy phenyl or 2-hydroxy phenyl. More preferably, when X is —NR'—, $R_1$ is 4-hydroxy phenyl. Alternatively, when X is —O—, $R_1$ is preferably a substituted or unsubstituted lower alkyl group, such as methyl, ethyl, propyl or benzyl.

In a preferred embodiment, the molecule is all-trans isomer. More preferably, the molecule is fenretinide which is an all-trans retinamide of Structural Formula (1), where X is —NH— and $R_1$ is 4-hydroxy phenyl.

Optionally, the retinamides or retinyl esters that disrupt the RBP4-TTR complex in circulation also bind intracellular retinoic acid receptors (RXRs) or peroxisome proliferators activator receptors (PPARs) to modulate their activity in a metabolically beneficial manner.

As used herein, the term "aliphatic group" is non-aromatic, consists solely of carbon and hydrogen and may optionally contain one or more units of unsaturation, e.g., double and/or triple bonds. An aliphatic group may be straight chained, branched, or cyclic (i.e., "cycloaliphatic"). When straight-chained or branched, an aliphatic group typically contains between about 1 and about 24 carbon atoms, more typically between about 1 and about 12 carbon atoms. Aliphatic groups are preferably lower alkyl groups or lower alkylene groups, which include C1-24 (preferably C1-C12) straight chained or branched saturated hydrocarbons. An alkyl group is a saturated hydrocarbon in a molecule that is bonded to one other group in the molecule through a single covalent bond from one of its carbon atoms. Examples of lower alkyl groups include methyl, ethyl, n-propyl, iso-propyl, n-butyl, sec-butyl and tert-butyl. An alkylene group is a saturated hydrocarbon in a molecule that is bonded to two other groups in the molecule through single covalent bonds from two of its carbon atoms. Examples of lower alkylene groups include methylene, ethylene, propylene, iso-propylene (—CH(CH2)CH2-), butylene, sec-butylene (—CH(CH3)CH2CH2-), and tert-butylene (—C(CH3)2CH2—).

As used herein, the term "aryl group" may be used interchangeably with "aryl," "aryl ring," "aromatic group," and "aromatic ring." Aromatic groups include carbocyclic aromatic groups and heteroaryl rings. Examples of carbocyclic aromatic groups include phenyl, 1-naphthyl, 2-naphthyl, 1-anthracyl and 2-anthacyl. The term "heteroaryl", "heteroaromatic", "heteroaryl ring", "heteroaryl group" and "heteroaromatic group" refer to heteroaromatic ring groups having five to fourteen members, including monocyclic heteroaromatic rings and polycyclic aromatic rings in which a monocyclic aromatic ring is fused to one or more other carbocyclic or heteroaromatic aromatic rings. Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

The term "non-aromatic heterocyclic group" refers to non-aromatic ring systems typically having five to fourteen members, preferably five to ten, in which one or more ring carbons, preferably one to four, are each replaced by a heteroatom such as N, O, or S. Examples of non-aromatic heterocyclic groups include 3-1H-benzimidazol-2-one, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, N-azetidinyl, 1-azetidinyl, 2-azetidinyl, N-oxazolidinyl, 2-oxazolidinyl, 4-oxazolidinyl, 5-oxazolidinyl, N-morpholinyl, 2-morpholinyl, 3-morpholinyl, N-thiomorpholinyl, 2-thiomorpholinyl, 3-thiomorpholinyl, N-pyrrolidinyl, 2-pyrrolidinyl, 3-pyrrolidinyl, N-piperazinyl, 2-piperazinyl, N-piperidinyl, 2-piperidinyl, 3-piperidinyl, 4-piperidinyl, N-pyrrolidinyl, 2-pyrrolidinyl, 3-pyrrolidinyl, 4-thiazolidinyl, diazolonyl, N-substituted diazolonyl, 1-pthalimidinyl, benzoxanyl, benzopyrrolidinyl, benzopiperidinyl, benzoxolanyl, benzothiolanyl, benzothianyl, tetrahydroquinolinyl, tetrahydroisoquinolinyl, azabicyclopentyl, azabicyclohexyl, azabicycloheptyl, azabicyclooctyl, azabicyclononyl, azabicyclodecyl, diazabicyclohexyl, diazabicycloheptyl, diazabicyclooctyl, diazabicyclononyl, and diazabicyclodecyl. Also included within the scope of the term "non-aromatic heterocyclic group", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring.

Suitable substituents on an aliphatic group, such as an alkyl or alkenyl group, and aryl group are those which do not substantially interfere with the inhibiting activity of the disclosed compounds, for example, binding RBP4 and disrupting RBP4-TTR complex in circulation. Examples of suitable substituents include —OH, halogens (—Br, —Cl, —I, —F), —OR$^a$, —O—COR$^a$, —COR$^a$, —CN, —NCS, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NR$^b$COR$^a$, —NHCONH$_2$, —NH-CONR$^a$H, —NHCON(R$^a$R$^b$), —NR$^b$CONH$_2$, —NR$^b$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$-C(=NR$^c$)—N(R$^a$R$^b$), —NHNH$_2$, —NHNHR$^a$, —NHR$^a$R$^b$, —SO$_2$NH$_2$, —SO$_2$NHR$^a$, —SO$_2$NR$^a$R$^b$, —SH, —SR$^a$, —S(O)R$^a$, and —S(O)$_2$R$^a$. In addition, an aliphatic group, such as an alkyl, or alkenyl group, can be substituted with substituted or unsubstituted aryl group to form, for example, an aralkyl group such as benzyl. Similarly, an aryl group can be substituted with a substituted or unsubstituted alkyl or alkenyl group.

R$^a$-R$^d$ are each independently an alkyl group, aromatic group, non-aromatic heterocyclic group or —N(R$^a$R$^b$), taken together, form a substituted or unsubstituted non-aromatic heterocyclic group.

Examples of molecules that interfere with the binding of the RBP4 and TTR include antibodies or fragments thereof that specifically bind to either RBP4 or TTR.

Additionally, pharmaceutically acceptable salts of the disclosed retinamides and retinyl esters are included in the present invention. For example, an acid salt of a compound containing an amine or other basic group can be obtained, by reacting the compound with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

Salts of compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-b-phenethylamine, dehydroabietylamine, N,N'-bisdehydroabietylamine, glucamine, N-methylglucamine, collidine, quinine, quinoline, and basic amino acid such as lysine and arginine.

The present invention includes pharmaceutical formulations of the compounds described herein. Pharmaceutical formulations can be adapted for administration by any appropriate route, for example by the oral (including buccal or sublingual), rectal, nasal, topical (including buccal, sublingual or transferal), vaginal or parenteral (including subcutaneous, intramuscular, intravenous or intradermal) route. Such formulations can be prepared by any method known in the art of pharmacy, for example by bringing into association the active ingredient with the carrier(s), diluent(s) or excipient(s).

Pharmaceutical formulations may be presented in unit dose forms containing a predetermined amount of active ingredient per unit dose. Such a unit may contain for example about 1 μg to 10 μg, about 0.01 mg to 1000 mg, or about 0.1 mg to 250 mg of the active ingredient, depending on the condition being treated, the route of administration and the age, weight and condition of the patient. In one embodiment, a retinamide, retinyl, or mimic thereof is administered orally, at a dose of about 10 to about 100 mg/day, or about 100 to about 500 mg/day or about 500 to about 1000 mg/day.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transferal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986).

Pharmaceutical formulations adapted for parenteral administration include aqueous and non-aqueous sterile injection solutions which may contain the antioxidants as well as buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Suitable pharmaceutical carriers or diluents are typically inert ingredients that do not significantly interact with the active components of a pharmaceutical composition. The carriers or diluents should be biocompatible, i.e., non-toxic, non-inflammatory, non-immunogenic and devoid of other undesired reactions at the administration site. One of ordinary skill in the art is readily able to select a carrier or diluent that is suitable for a particular method of administration or for a particular type of pharmaceutical composition (e.g., one containing retinamide or retinyl ester). Examples of pharmaceutically acceptable carriers and diluents include, for example, sterile water, physiological saline, bacteriostatic saline (saline containing about 0.9 mg/ml benzyl alcohol), phosphate-buffered saline, Hank's solution, Ringer's lactate, commercially available inert gels, or liquids supplemented with albumin, methyl cellulose or a collagen matrix. Additional carriers and diluents include sugars such as lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added (e.g., to a tablet or capsule), such as the cross-linked polyvinyl pyrrolidone, agar, or alginic acid or a salt thereof such as sodium alginate. Other carriers and diluents are described in Remington's Pharmaceutical Sciences, Mack Publishing Company, Easton, Pa., the contents of which are incorporated by reference.

Pharmaceutical compositions of the invention can be prepared by combining, for example a retinamide or retinyl ester disclosed herein and a pharmaceutically active agent, and optionally including one of the carriers of diluents described above. Also included in the present invention are pharmaceutically acceptable salts of the disclosed compounds. Depending on the charge of the compound, a salt will contain a positive ion or negative ion as a counterion. Compounds that have both a phosphate group and an amine group are considered to have no excess charge. In this case, phosphate and amine groups can serve as counterions for each other or each group can have an exogenous counterion. Suitable cations include alkaline earth metal ions, such as sodium and potassium ions, alkaline earth ions, such as calcium and magnesium ions, and unsubstituted and substituted (primary, secondary, tertiary and quaternary) ammonium ions. Pharmaceutically acceptable counter anions include chloride, bromide, acetate, formate, citrate, ascorbate, sulfate and phosphate.

As used herein, the term "therapeutically effective amount" means the amount needed to achieve the desired therapeutic or diagnostic effect or efficacy. The actual effective amounts of drug can vary according to the biological activity of the particular compound employed; specific drug or combination thereof being utilized; the particular composition formulated; the mode of administration; the age, weight, and condition of the patient; the nature and severity of the symptoms or condition being treated; the frequency of treatment; the administration of other therapies; and the effect desired. Dosages for a particular patient can be determined by one of ordinary skill in the art using conventional considerations (e.g. by means of an appropriate, conventional pharmacological protocol).

For general information concerning formulations, see e.g., Gilman, et al. (eds.), 1990, *Goodman and Gilman's: The Pharmacological Basis of Therapeutics,* 8th ed., Pergamon Press; and *Remington's Pharmaceutical Sciences,* 17th ed., 1990, Mack Publishing Co., Easton, Pa.; Avis, et al. (eds.), 1993, *Pharmaceutical Dosage Forms: Parenteral Medications,* Dekker, New York; Lieberman, et al. (eds.), 1990, *Pharmaceutical Dosage Forms: Disperse Systems,* Dekker, New York. The compounds of the present invention can be administered in conventional pharmaceutical administration forms, for example, uncoated or (film-)coated tablets, capsules, powders, granules, suppositories, suspensions or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, and/or antioxidants (cf. H. Sücker, et al., Pharmazeutische Technologie, Thieme-Verlag, Stuttgart, 1978). The administration forms obtained in this way typically contain from about 1 to about 90 percent by weight of the active substance.

Methods of Reducing Insulin Resistance in an Individual

RBP4 is a circulatory protein that is produced, for example by hepatocytes and adipocytes. RPB4 is part of an extracellular transport system for retinol. RBP4 is synthesized in an apo form in the rough endoplasmic reticulum. However, RBP4 is not efficiently transferred out of the endoplasmic reticulum until it is complexed with retinol. Furthermore, RBP4 is predominately found in the serum bound to a homotetrameric protein, transthyretin (TTR). TTR itself can bind two molecules of thyroid protein, but in the context of retinol homeostasis, is thought to prevent the 21 kDa RBP4 from being excreted during plasma filtration in the kidney. Therefore, the activity level of RBP4 can be altered by changing the level of RBP4 produced or maintained in the body, which in turn can be altered by changing 1) the rate of production of nascent RBP4, 2) the ability of RBP4 to interact with retinol, 3) the ability of RBP4 to interact with TTR and 4) the half life of RBP4 in the body. In addition, RBP4 activity can be altered by changing the ability of RBP4 to deliver retinol to the cells such that, for example, retinol dependent signaling is affected.

Specifically encompassed herein are methods for reducing insulin resistance in a mammal, including humans, comprising administering to a mammal a compound that reduces RBP4 activity. In one embodiment, the mammal has at least one clinical symptom of insulin resistance. In a particular embodiment, the compound causes reduction in circulating RBP4 when administered to the individual in sufficient amount. Reduction in RBP4 levels can be any statistically significant percentage reduction in RBP4 levels, for example by at least about 20% of the difference between levels found in the insulin resistant state and levels associated with the non-insulin state, as adjusted for age, gender, and ethnicity of the individual. In more particular embodiments, the level of RBP4 is reduced by at least about 30, or 40, or 50, or 60, or 70% of the difference between levels found in the insulin resistant state and levels associated with the non-insulin state, as adjusted for age, gender, and ethnicity of the individual. In particular, the RBP4 levels in an individual with known insulin resistance or related condition are elevated above levels normally associated with the non-insulin resistant state, as adjusted for age gender and ethnicity, based on RBP4 immunoreactivity (ELISA, RIA, nephlometry, Western blotting) in tissues or circulation, and reduced, for example, by about 40%-60%, or about 50% of the difference between the individual's level and the levels associated with the non-insulin resistant state. Using the molecules/methods described herein levels of activities of RBP4 associated with insulin resistance are returned to levels of activities associated with the non-insulin resistant state.

Also encompassed by the present invention are methods of treating insulin-resistance and related conditions. In particular, methods of reducing insulin resistance in an individual comprise administering to the individual a compound that reduces or inhibits or antagonizes the activity of RBP4, e.g., a test compound that antagonizes RBP4 activity. RBP4 activity is described above and includes: ability to bind retinol, ability to interact with transthyretin, ability to deliver retinol to tissues and influence levels of biologically active retinoids in tissues and circulation—including but not limited to all trans retinoic acid, 9-cis-retinoic acid, 11-cis-retinoic acid, 13-cis-retinoic acid, all trans retinal, 9-cis-retinal, 11-cis-retinal, 13-cis-retinal, corresponding isomeric metabolites, and retinyl esters—and ability to influence activation of nuclear hormone receptors by regulation of retinoid levels in tissues resulting in altered regulation of PPAR_-RXR, RAR-RXR, RXR-RXR, LXR-RXR and any nuclear hormone receptor or other signal transduction molecule that interacts directly or indirectly with RAR or RXR. The possession of any one, or more than one, of these activities defines a biologically active RBP4 protein or protein fragment. Reduction of any of these activities associated with insulin resistance in the presence of the test compound, as compared to the activity in the absence of the test compound, is indicative of a compound that antagonizes activity of RBP4 and thereby reduces insulin resistance.

In particular, in one embodiment, the plasma level of RBP4 is lowered, for example, by interfering with RBP4 binding to transthyretin to promote RBP4 excretion.

In another embodiment plasma levels of RBP4 are lowered by reducing RBP4 gene expression. Such methods can encompass methods that reduce or inhibit the expression of RBP4 mRNA, or the translation of RBP4 gene into active RBP4 protein, such as using RNAi or anti-sense polynucleotides. Also encompassed herein are methods that inhibit or reduce the ability of RBP4 to bind to cells, or to its carrier protein, transthyretin. Such methods can include the use of antibodies (intact or fragments thereof) that specifically bind to RBP4 and prevent the protein from binding to the cell or transthyretin. Other molecules identified by the screening methods described herein can also be suitable for reducing insulin-resistance, such as small molecules that inhibit/reduce the biological activity of RBP4. In particular, the present invention covers small molecules/drugs that interfere with the binding of RBP4 to transthryetin, resulting in increased renal clearance (i.e., excretion in the urine) of circulating RBP4. Such small molecules can, for example, compete for the binding sites/receptors of RBP4 and thus, inhibit the binding of RBP4 to the cell/receptor/carrier protein. Such small molecules include the retinamides and retinyl esters described herein. Retinamides or retinyl esters can be administered to the mammal as described herein for fenretinide.

The compounds and pharmaceutical compositions as described herein can be administered by an appropriate route. Suitable routes of administration include, but are not limited to, orally, intraperitoneally, subcutaneously, intramuscularly, transdermally, rectally, sublingually, intravenously, buccally or via inhalation. Preferably, compounds and pharmaceutical compositions of the invention are administered orally. For example, retinamides and retinyl esters are expected to be bioavailable when taken orally. Pharmaceutical excipients known to enhance bioavailability of compounds administered orally can be added to the compound.

Diagnostic Methods

Also encompassed by the present invention are methods of diagnosing insulin-resistance or related conditions, such as Metabolic Syndrome, in a mammal (e.g., a human) using a specific insulin-resistance/Metabolic Syndrome surrogate marker, wherein the marker is RBP4 protein, or a fragment thereof (for example a biologically active fragment or characteristic fragment).

Also encompassed by the present invention are methods for diagnosing insulin resistance in an individual, comprising measuring the amount of RBP4 in a biological sample obtained from an individual, wherein an elevated level of RBP4 in the biological sample compared to a control sample normalized for age, gender, ethnicity, and (possibly) body mass index is indicative of insulin resistance. The biological sample can be any suitable sample, but in particular, is a blood serum sample or tissue sample (e.g. muscle or adipose). The detection of an elevated level of RBP4 relative to normal levels of RBP4 in the biological sample is an indication of insulin resistance, or a related condition. Any statistically significant elevation of RBP4 levels is encompassed by the present method. For example, a measurement of at least about 1.3-fold to about 1.5-fold, or 2-fold or greater RBP4 level than would be found in non-insulin resistant individuals is an elevated level.

An individual could be screened and diagnosed for insulin resistance using elevated RBP4 protein levels as a marker. RBP4 levels could be assayed from a biological sample, preferably a blood sample, by placing a drop of blood on a piece of filter paper and using an anti-RBP4 antibody to detect and quantitate the amount of RBP4. The filter paper can be stored at room temperature and RBP4 levels remain stable for the assay. See Craft, *J. Nutr.* 131:1626S-1630S (2001). Such methods are especially suitable for mass screenings. Such diagnostic methods can utilize antibodies, or fragments thereof, that specifically bind to RBP4, or methods of detecting RBP4 RNA or DNA.

RBP4 protein expression level can also be measured by in vitro techniques described herein. The rate of translation and turnover of the protein can be determined in cells by performing a pulse-chase assay and by using a drug like cycloheximide that inhibits protein translation. In vivo, protein detection can be accomplished by introducing a labeled (i.e. radioactive) anti-RBP4 antibody into a subject and then visualizing the label using standard imaging techniques. Other suitable assays for diagnosing insulin resistance by detecting RBP4 activity are described above.

The target population for screening includes people with obesity, the Metabolic Syndrome, dyslipidemia, history of gestational diabetes, impaired fasting glucose, impaired glucose tolerance, and Type 2 diabetes. This includes a rapidly growing pediatric population with obesity and Type 2 diabetes.

The present invention will be more particularly described in the following examples, which are not meant to be limiting in any way.

Exemplification

I. A Mouse Model for Insulin Resistance

A. Adipose Tissue Glucose Transporter 4 (GLUT4) Knock Out Mice (AG4KO) and Adipose Tissue Glut4 Overexpressor Mice (G4A$^+$)

Cre/LoxP DNA recombination was used to generate mice with adipose-selective knockout of the glucose transporter, GLUT4. Transgenic mice containing the GLUT4 gene surrounded by LoxP sites were crossed with transgenic mice expressing CRE recombinase selectively in adipose tissue.

Figure 1:
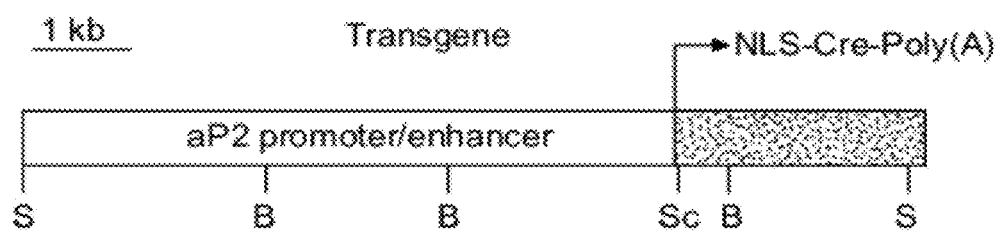
FIG. 1 is a schematic diagram of the aP2-Cre transgene construct.
Figure 2:
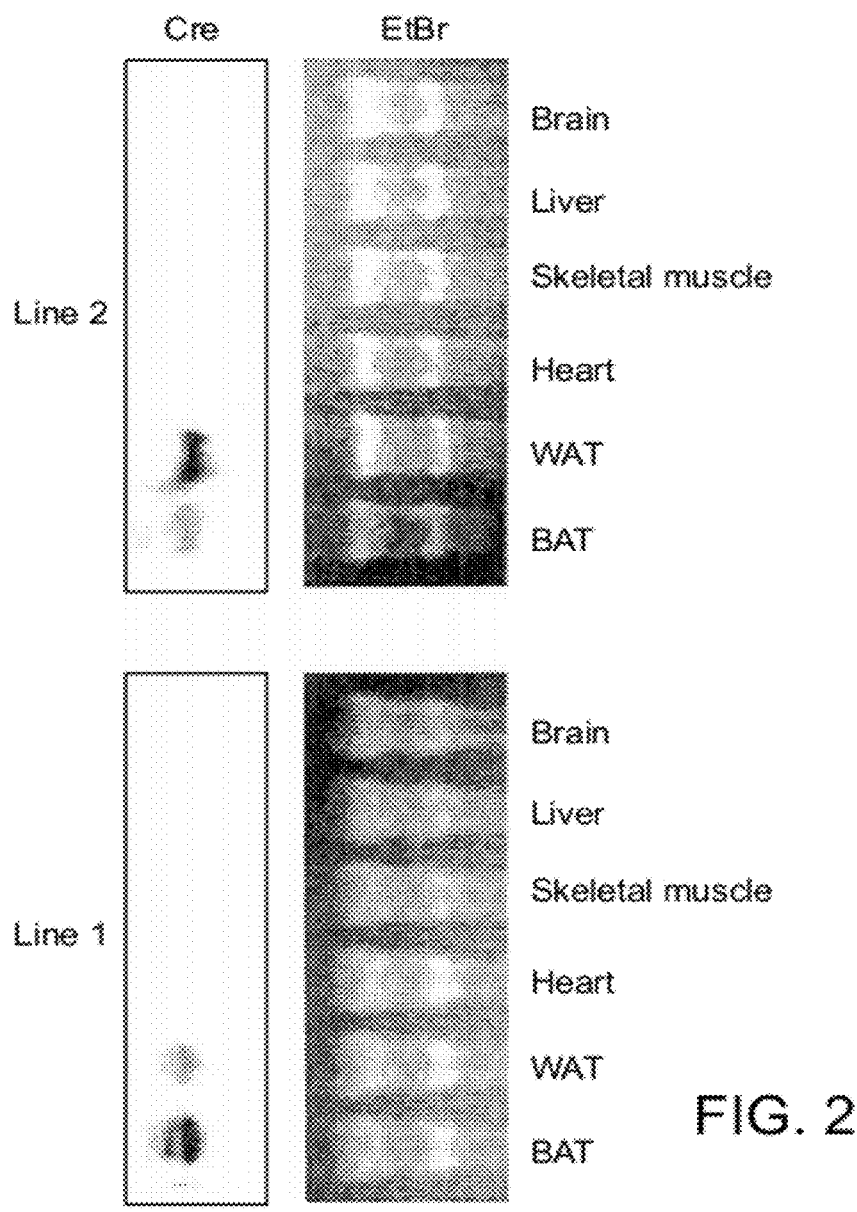
FIG. 2 shows representative northern blots demonstrating that CRE expression is limited to brown and white adipose tissue (BAT and WAT, respectively) in two independent lines of transgenic mice.

Adipose-specific expression of CRE recombinase was achieved by ligating aP2, an adipose specific promoter, to the Cre gene. The aP2-Cre transgene was made by cloning a 1.4-kb SacI/SalI complementary DNA fragment encoding CRE recombinase, modified by inclusion of a nuclear localization sequence (NLS) and containing a consensus polyadenylation signal, immediately downstream of the 5.4 kb promoter/enhancer of the fatty-acid-binding protein aP2. (FIG. 1). The construct was injected into male pro-nuclei of mouse zygotes from the FVB mouse strain. Two lines of aP2-CRE mice were examined. In both lines, CRE expression was restricted to brown adipose tissue (BAT) and white adipose tissue (WAT) (FIG. 2).

Figure 3:
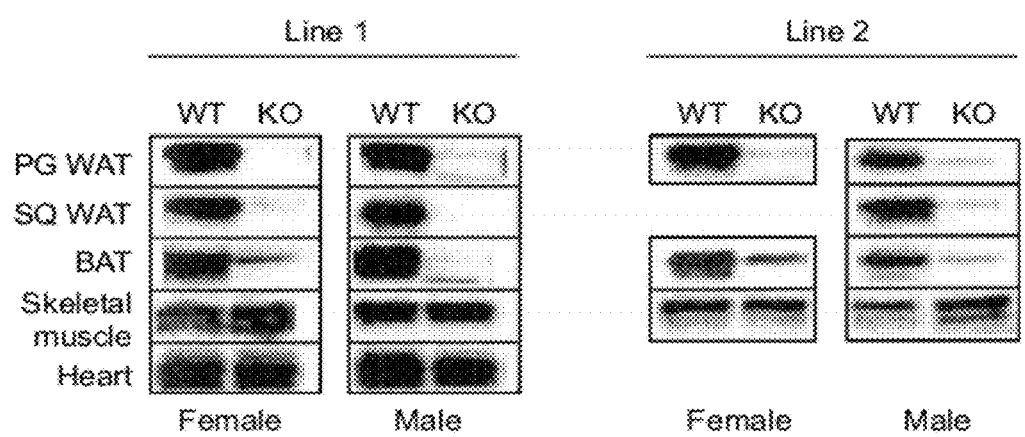
FIG. 3 shows representative immunoblots of GLUT4 in perigonadal (PG) and subcutaneous (SQ), WAT and BAT, gastrocnemius skeletal muscle and heart of wildtype (WT) and GLUT 4 adipose knockout mice (AG4KO) from both aP2-Cre transgenic lines.

AG4KO mice were derived by crossing GLUT4 LoxP heterozygous mice with the CRE expressing mice described above. AG4KO mice have the genotype CRE Lox/Lox and were born with the expected Mendelian frequency. Thus, absence of adipose GLUT4 caused no embryonic lethality. GLUT4 protein levels were reduced by 70-99% in both BAT and WAT (epididymal, periovarian and subcutaneous) of male and female AG4KO mice (FIG. 3) generated with either line of aP2-CRE mice. In both AG4KO lines, GLUT4 expression was preserved in skeletal muscle and heart (FIG. 3). Transgenic mice over expressing GLUT4 in adipose tissue were made as described in Shepard, et al., *J. Biol. Chem.* 268:22243 (1993).

B. AG4KO are Normal with Respect to Global Fat Levels and Overall Weight

Figure 4C:
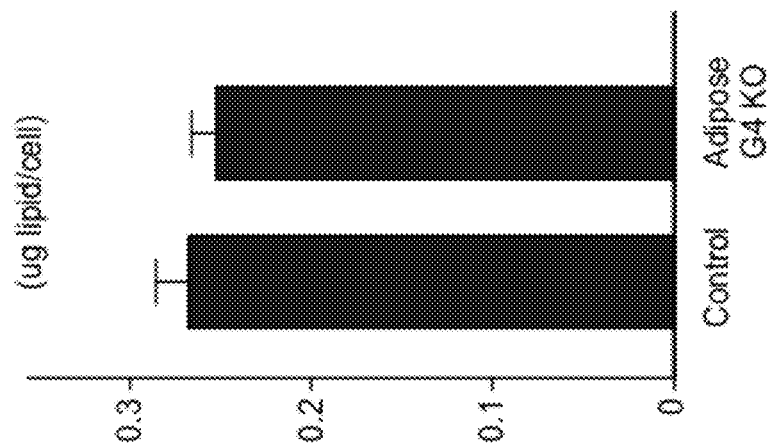
FIG. 4C is a bar graph comparing adipocyte size in μg lipid/cell in control (left bar) in AG4KO mice (right bar).
Figure 4B:
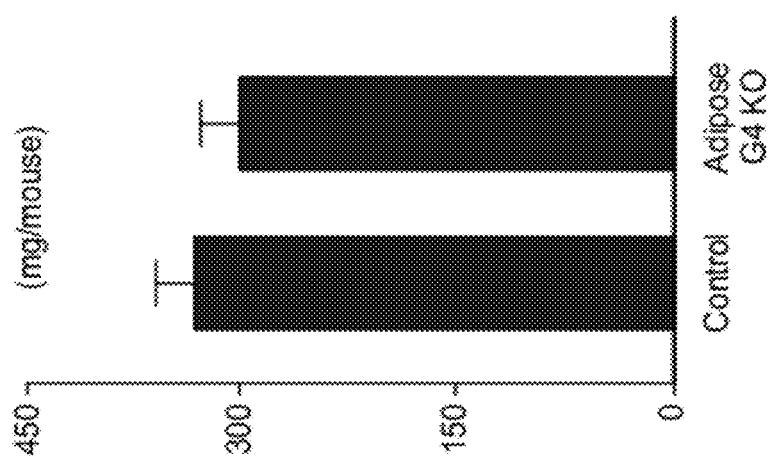
FIG. 4B is a bar graph showing the gonadal fat pad weight in mg/mouse in control (left bar) and AG4KO mice (right bar).
Figure 4A:
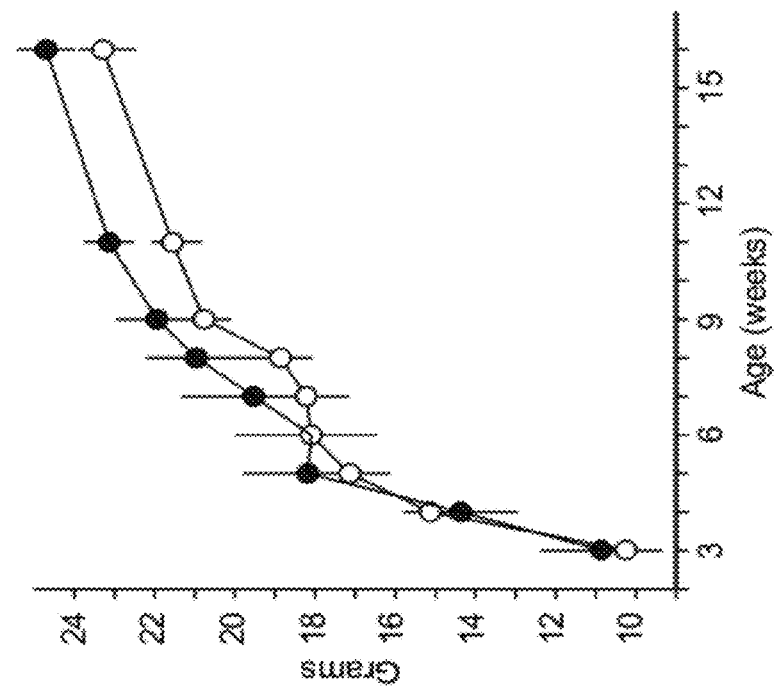
FIG. 4A is a growth curve in grams versus age (weeks) showing that AG4KO mice (dark circles) have normal growth compared to WT mice (light circles).

As shown in FIG. 4A, growth curves of male and female AG4KO mice were similar to wildtype from 3-16 weeks of age. Fat pad weights and adipocyte size in AG4KO mice were also similar to wild type (FIG. 4B and FIG. 4C, respectively). In addition, adipocyte morphology is homogeneous in AG4KO mice. Thus, reduction of GLUT4 selectively in adipose tissue does not result in growth retardation or decreased adipose mass or adipose size. Heart weight in AG4KO mice was also similar to wild type.

C. AG4KO Mice are Normal with Respect to Skeletal Muscle GLUT4 and Glucose Transport Ex Vivo As shown in FIG. 5A, GLUT4 expression in skeletal muscle of AG4KO mice is similar to wild type. GLUT4 expression was measured by immunoblotting. Tissue was extracted and homogenized using a medium Polytron setting and buffer (HEPES 50 mM Triton® X-100 (polyoxyethylene) 1%, sodium pyrophosphate 50 mM, NaF 100 mM, EDTA 10 mM, vanadate 10 mM, aprotinin 10 µg/ml, leupeptin 10 µg/ml, benzamidine 2 mM). After initial centrifugation at 13,000 g, the supernatant was then centrifuged at 100,000 g for 1 hour at 4° C. The resultant supernatant was used for immunoblotting according to Abel, et al., *J. Clin. Invest.*, 104:1703-1714 (1999).

Figure 5B:
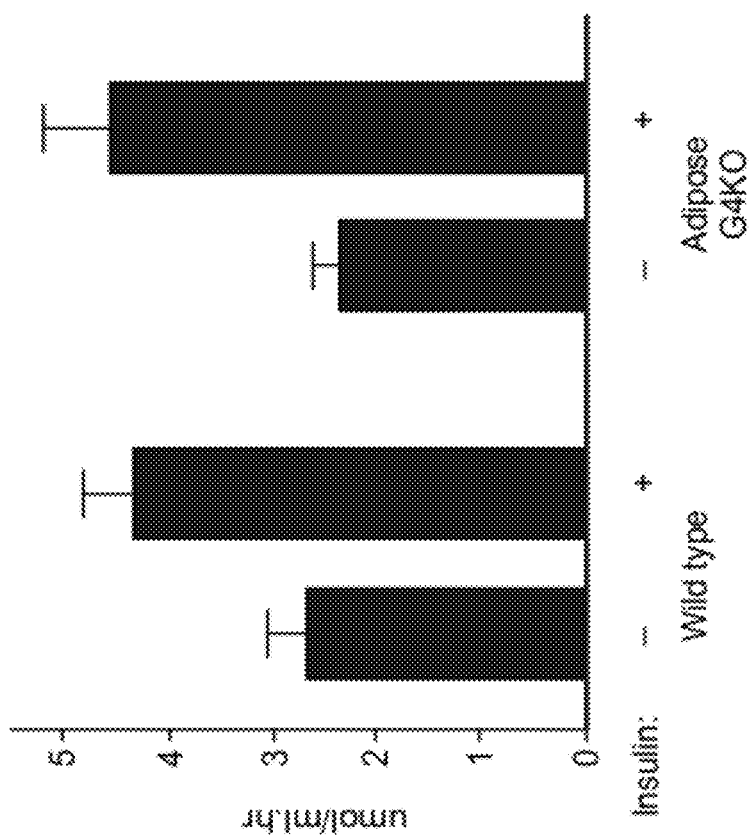
FIG. 5B is a bar graph showing basal and insulin-stimulated glucose uptake in isolated muscle of AG4KO mice (N=5) in WT mice (N=5).
Figure 5A:
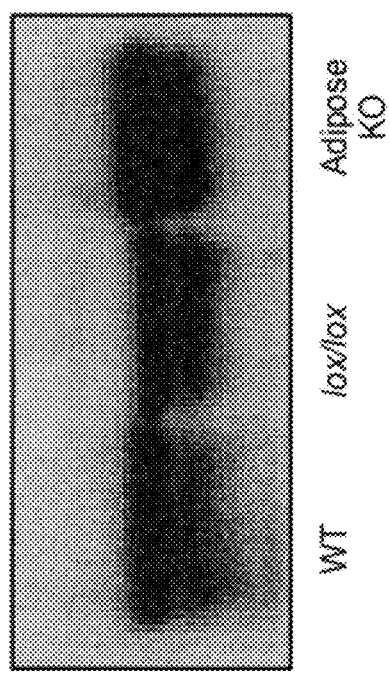
FIG. 5A is an immunoblot showing GLUT4 content from WT, Lox/Lox, and AG4KO mice.

In addition, basal and insulin-stimulated glucose transport in AG4KO skeletal muscle were similar to wild type when ed ex vivo (FIG. 5B). To measure glucose transport ex vivo, mice were fasted overnight, and killed by $CO_2$ inhalation. Skeletal muscle was rapidly dissected and glucose transport measured according to Zisman, et al., *Nature Med.*, 6:924-928 (2000).

D. AG4KO Mice are Insulin Resistant (IR) but G4A$^+$ Mice are Not

Figure 6B:
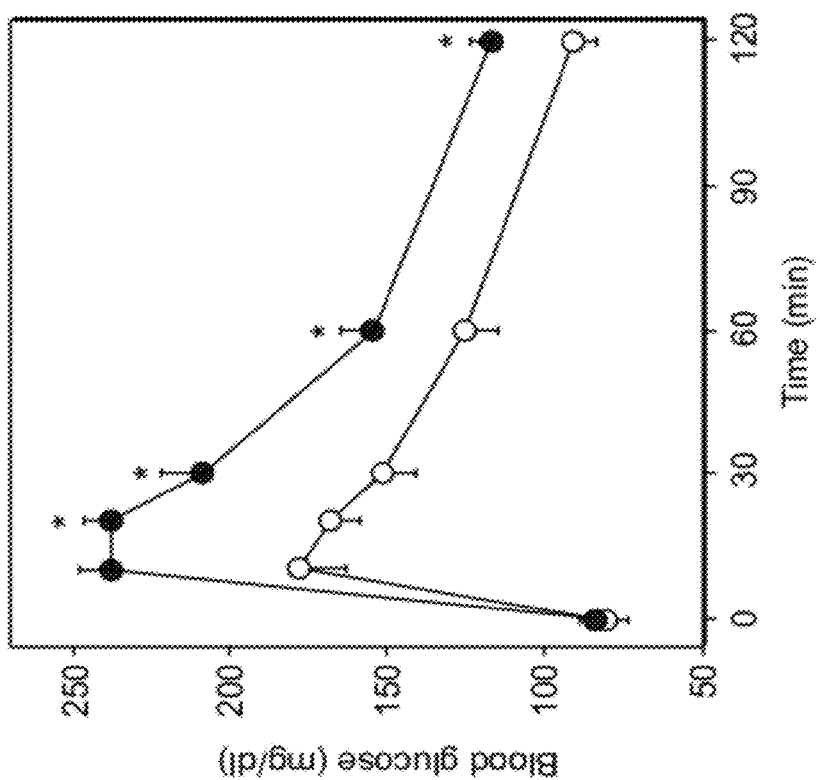
FIG. 6B shows clearance of blood glucose (glucose tolerance test, GTT) (1 mg/kg) after injection of 1 mg glucose per kg body weight (i.p.) in AG4KO mice (filled circles) and WT controls (open circles).
Figure 6A:
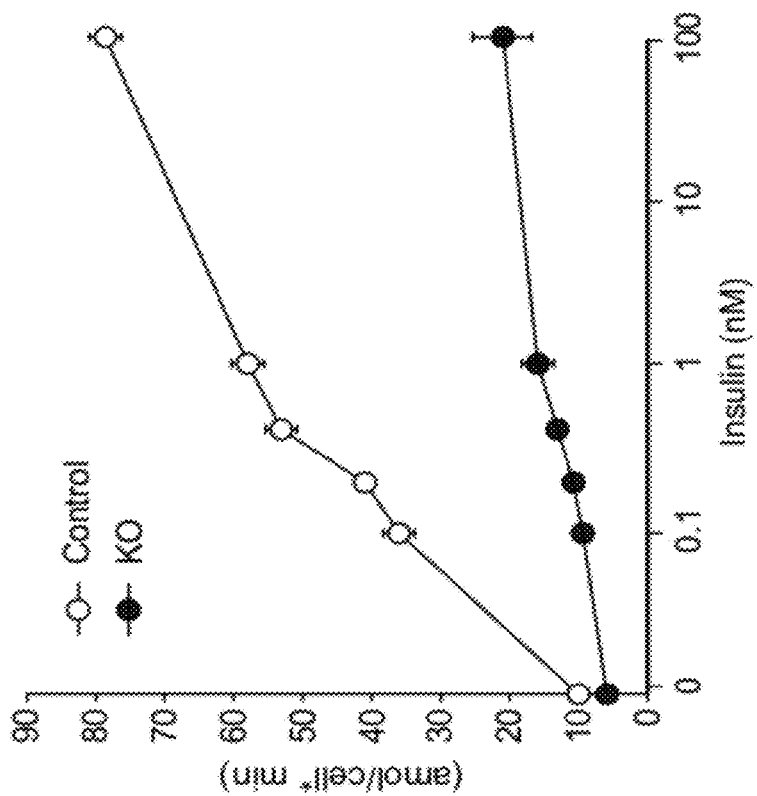
FIG. 6A shows a dose response curve for insulin-stimulated glucose uptake in isolated adipocytes from AG4KO mice (closed circles) and control mice (open circles).

As shown in FIG. 6A, glucose uptake in AG4KO adipocytes is impaired. To measure glucose transport, adipocytes were isolated from periovarian or epididymal fat pads from fed mice by collaginase digestion (1 mg/ml). Glucose transport was measured according to Satou, Y. and Satou, N., *Dev. Biol.*, 192:467-481 (1997).

As shown in FIG. 6B, glucose tolerance is impaired in AG4KO mice. Glucose tolerance tests were performed in awake mice after a twelve-hour fast according to Abel, et al., (Id.).

As demonstrated by the euglycemic clamp technique, adipose-specific GLUT4 knockout causes insulin resistance. FIG. 7A shows insulin-stimulated whole body glucose uptake in control and AG4KO mice. Euglycemic clamp studies measuring uptake of [$^{14}$C] 2-deoxyglucose into individual tissues were performed as described by Kim, et al., *J. Bio. Chem.*, 275:8456-8460 (2000). The data shown are means+/−S.E.M. for 5-6 mice per genotype (* is P<0.05 versus control). Insulin-stimulated whole body glucose uptake was decreased by 53% in AG4KO mice.

Figure 7B:
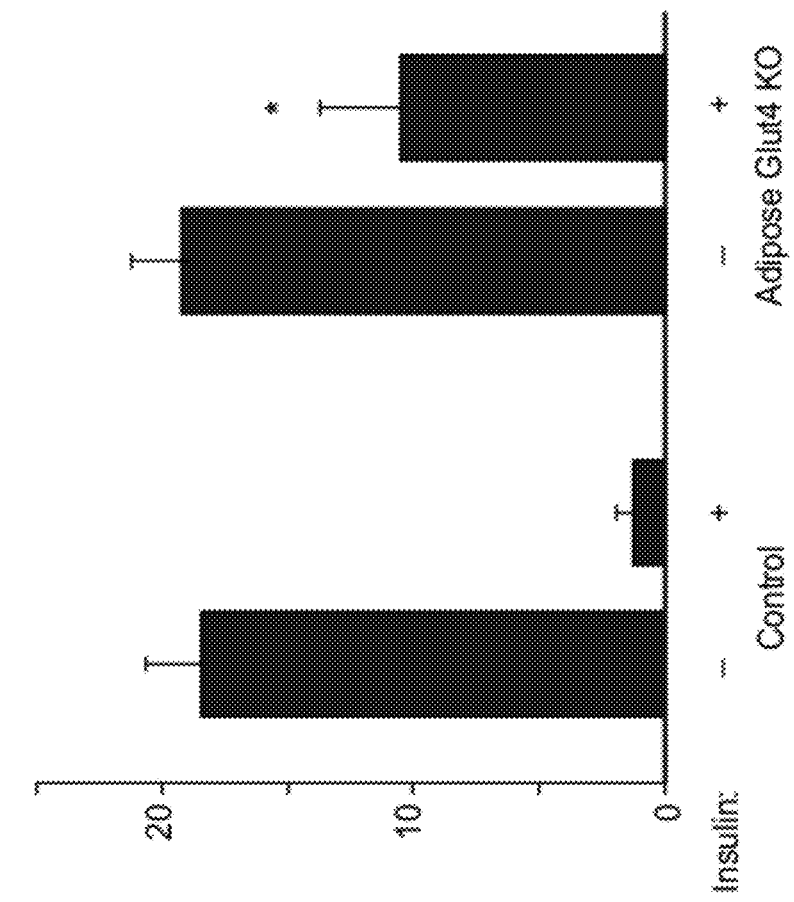
FIG. 7B shows hepatic glucose production in the presence or absence of insulin in control (left bars) and AG4KO mice (right bars).
Figure 7A:
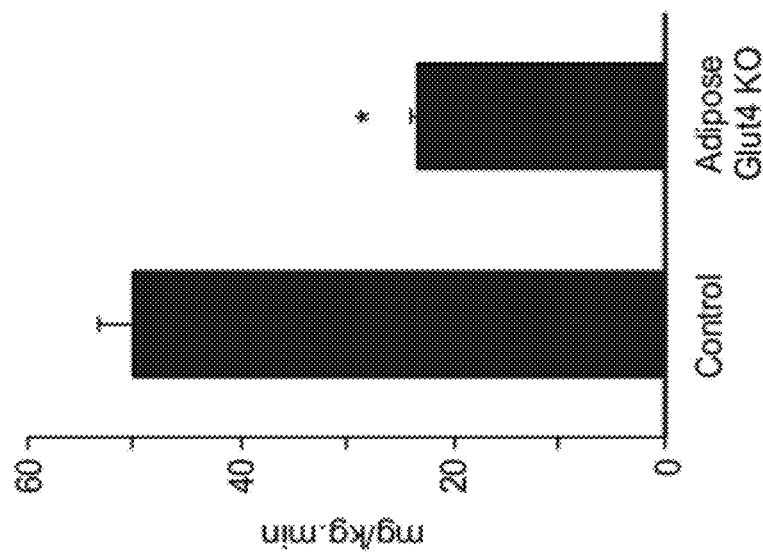
FIG. 7A shows insulin-stimulated whole body glucose uptake in control (left bar) and AG4KO mice (right bar).

Hepatic glucose production in AG4KO mice was similar to wild type in the basal state, but the ability of insulin to suppress hepatic glucose production was severely impaired in AG4KO mice (FIG. 7B).

As shown in FIGS. 8A and 8B, insulin-stimulated glucose transport into WAT and BAT of AG4KO mice was markedly reduced in vivo. However, unexpectedly, glucose transport into skeletal muscle of AG4KO mice was also impaired by about 40% in vivo, (FIG. 8C) in spite of preserved expression of GLUT4 in muscle (FIG. 2). Glucose uptake was measured as described in Kim, et al., (Id.).

II. AG4KO Mice have Elevated Serum RBP4

A. Insulin Resistance in AG4KO Mice is Mediated by a Secreted Factor

Figure 9:
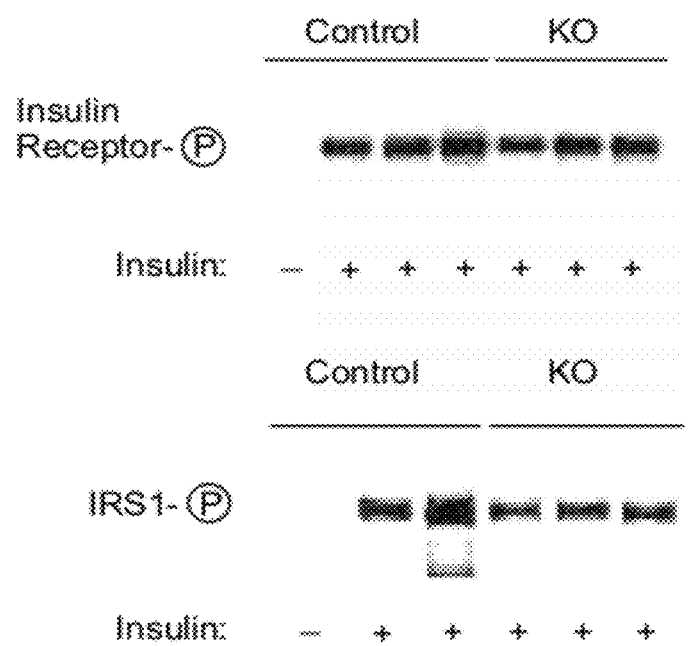
FIG. 9 shows immunoblots of insulin-stimulated phosphorylation of the insulin receptor (top panel) or Insulin Receptor Substitute-1 (IRS1) (bottom panel) from control (left column set) and AG4KO mice (right column set).

Insulin signaling is impaired in muscle of AG4KO mice. As demonstrated by FIG. 9, insulin resistance was also present at the level of activation of the insulin receptor and IRS 1 (FIG. 9), signaling steps that are necessary for activation of GLUT4.

Figure 10:
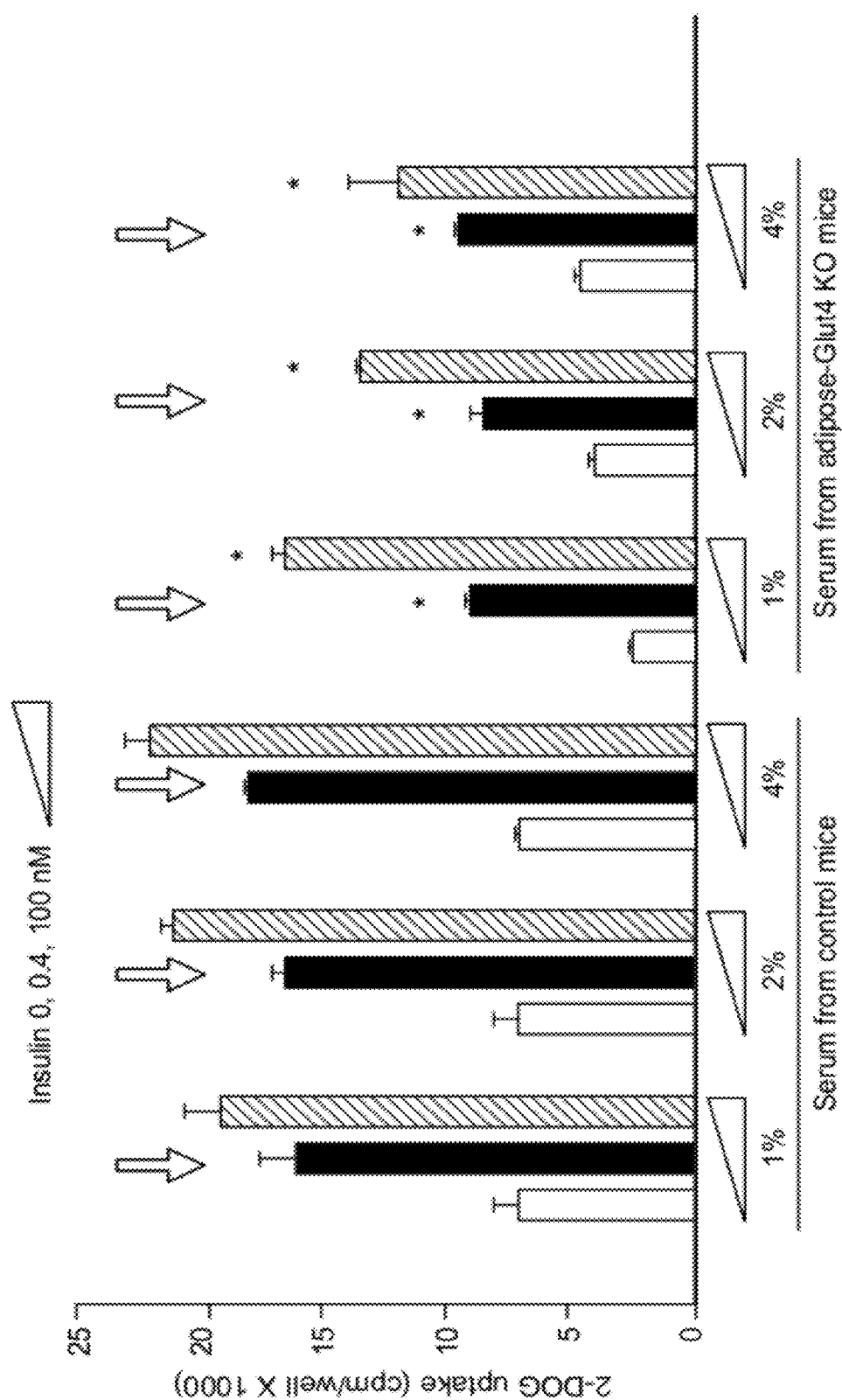
FIG. 10 shows insulin-stimulated 2-deoxyglucose uptake in 3T3-L1 adipocytes in the presence increasing concentrations of either serum from control mice (left group) or serum from AG4KO mice (right group).
Figure 16:
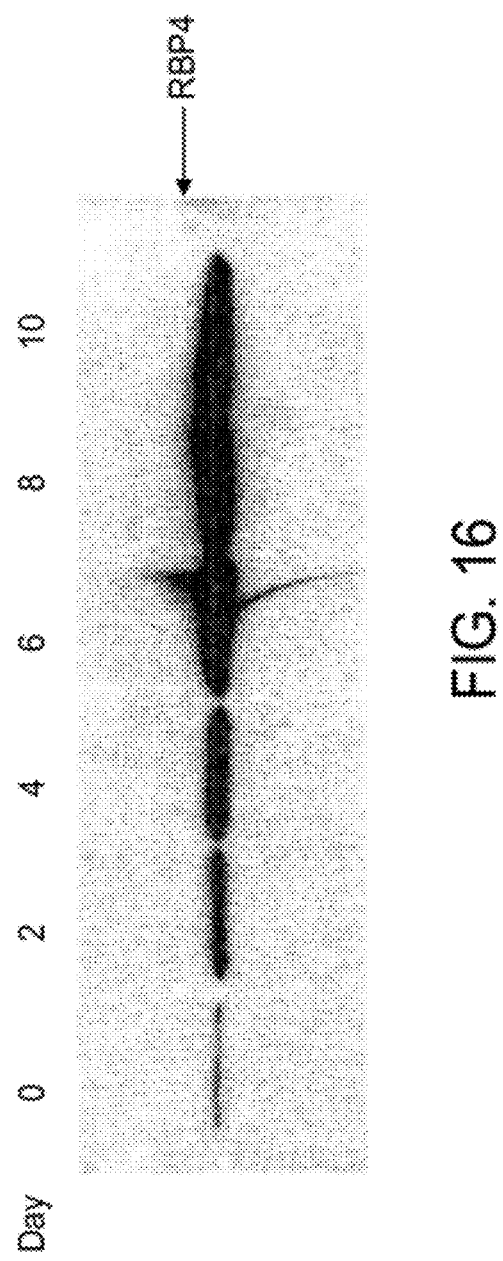
FIG. 16 shows an immunoblot of RBP4 at the indicated day after induction of differentiation of 3T3-L1 cells.
Figure 17B:
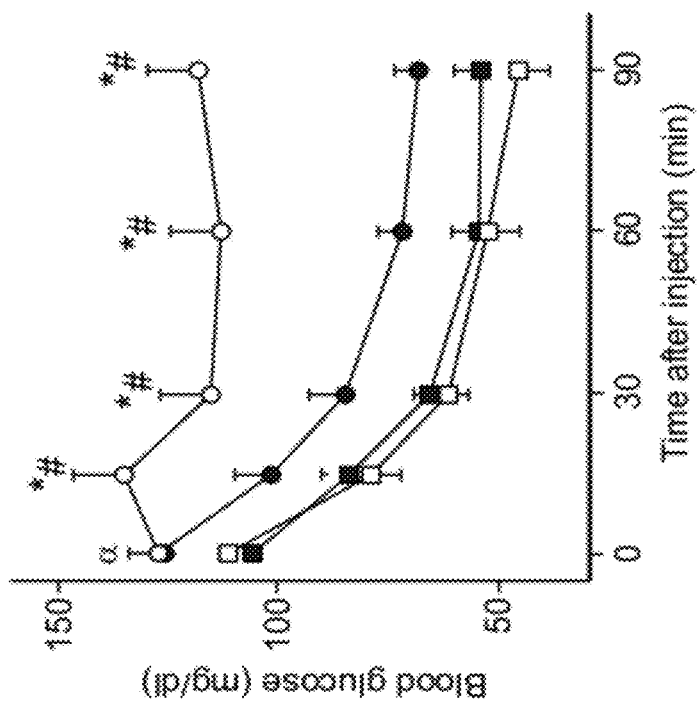
FIG. 17B shows blood glucose as a function of time after i.p. injection with insulin (0.75 U/kg body weight, insulin tolerance test, ITT) in AG4KO mice before (open circles) and after (closed circles) treatment with TZD compared to control mice before (closed squares) and after (open squares) treatment with TZD.
Figure 17A:
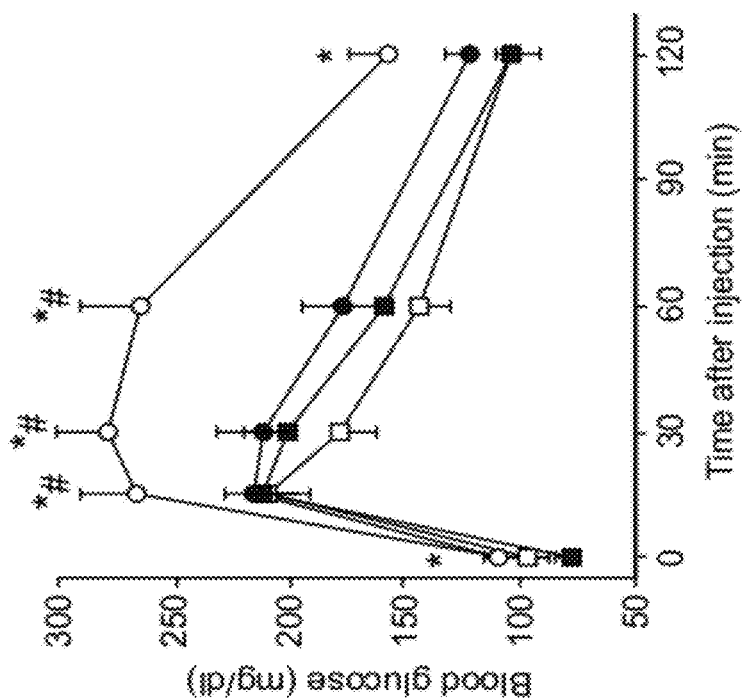
FIG. 17A shows blood glucose level after glucose i.p. injection (1 mg/kg body weight GTT) in AG4KO mice before (open circles) and after (closed circles) treatment with a thiazolidindione class of drug (TZD), compared to control mice before (closed squares) and after (open squares) treatment with TZD.

Serum from AG4KO mice inhibits glucose transport in 3T3-L1 adipocytes. 2-deoxyglucose uptake was measured in 3T3-L1 adipocytes that had been treated with either serum from control (FVB) mice or serum from AG4KO mice in the presence of increasing concentrations of insulin. As shown in FIG. 10, serum from AG4KO mice inhibited the uptake of 2-deoxyglucose by 3T3-L1 adipocytes in response to insulin, demonstrating the presence of a secreted factor in AG4KO serum that mediates insulin resistance. Interestingly, expression of RBP4 is induced during differentiation of 3T3-L1 cells (FIG. 16).

B. Identification of RBP4

Figure 11:
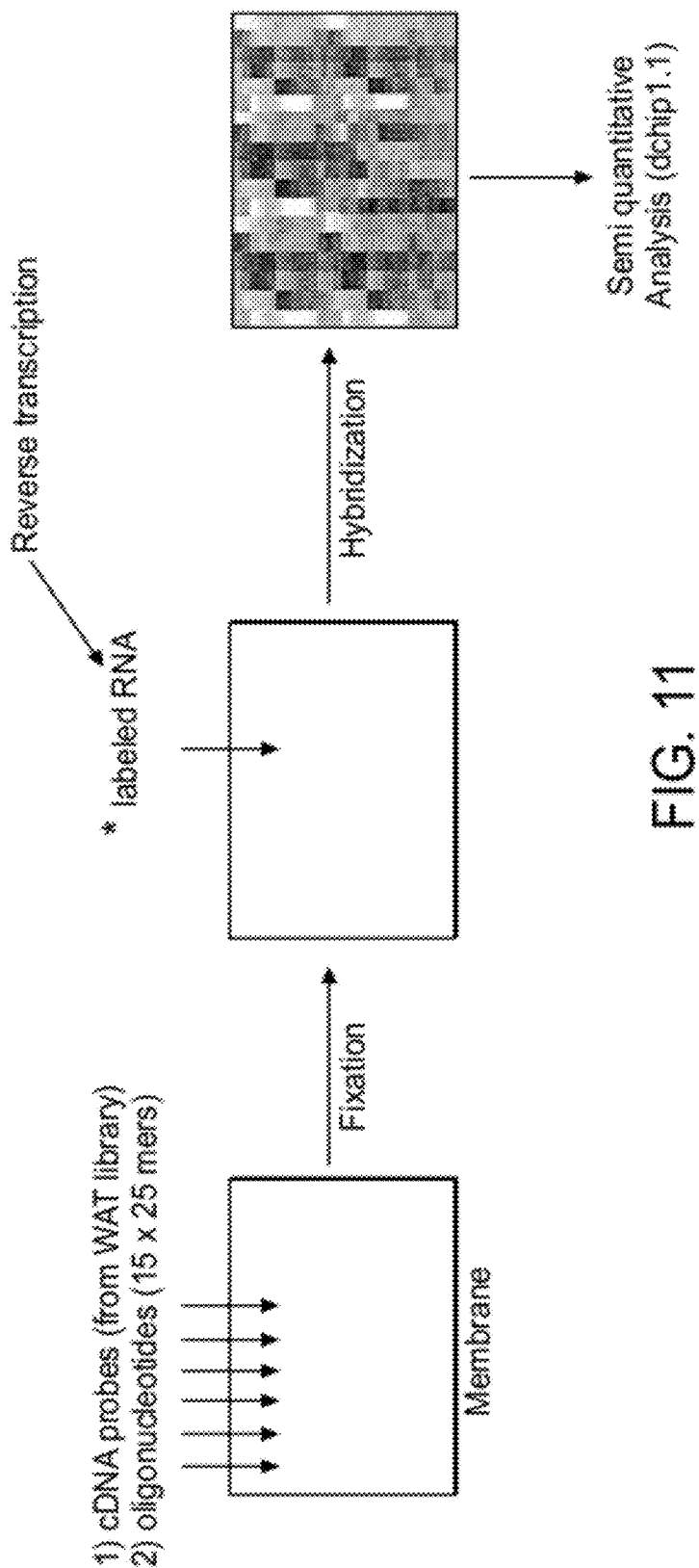
FIG. 11 shows a schematic of the microarray analysis of white adipose tissue (WAT) RNA.

In order to identify the serum factor involved in the insulin resistance phenotype of AG4KO mice, microarray analysis of WAT RNA was conducted. FIG. 11 shows a schematic of the microarray analysis. Total RNA from white adipose tissue was extracted using RNeasy® Mini Kit (Qiagen, Valencia, Calif.). Labeled adipose tissue RNA was incubated with mouse oligonucleotides (MG-U74A v.2, Affymetrix) under hybridizing conditions. Mouse RBP4 mRNA was quantified with real time PCR using TaqMan® One-step RT-PCR Master Mix (Applied Biosystems) and the following primer/probe set: (forward) SEQ ID NO: 1 TCTGTGGAC-GAGAAGGGTCAT, (reverse) SEQ ID NO: 2 CCAGTTGCTCAGAAGACGGAC, and (probe) SEQ ID NO: 3 TGAGCGCCACAGCCAAGGGAC.

Figure 12:
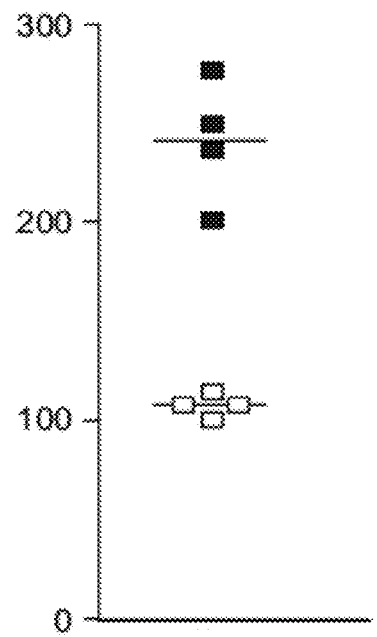
FIG. 12 shows RBP4 mRNA level determined by rt-PCR derived from WAT from wild type mice (open squares) and from AG4KO mice (closed squares); the lines indicate the average value for each group.
Figure 13:
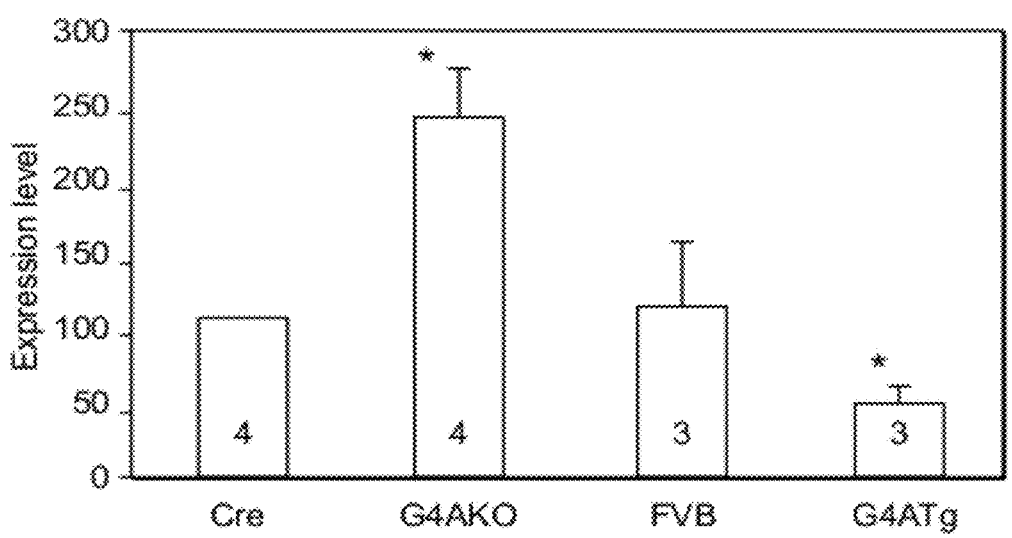
FIG. 13 shows RBP4 mRNA expression level in G4AKO (mice (left middle bar) Cre mice (left bar), control mice (right middle bar) and GLUT4 over expressing mice (right bar).
Figure 14:
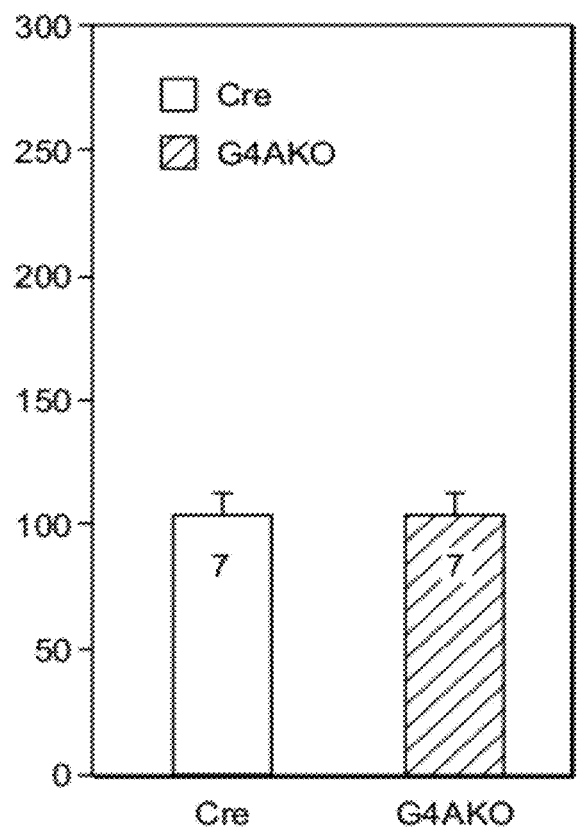
FIG. 14 shows RBP4 mRNA expression level in the liver of control (left bar) and AG4KO mice (right bar).
Figure 15A:
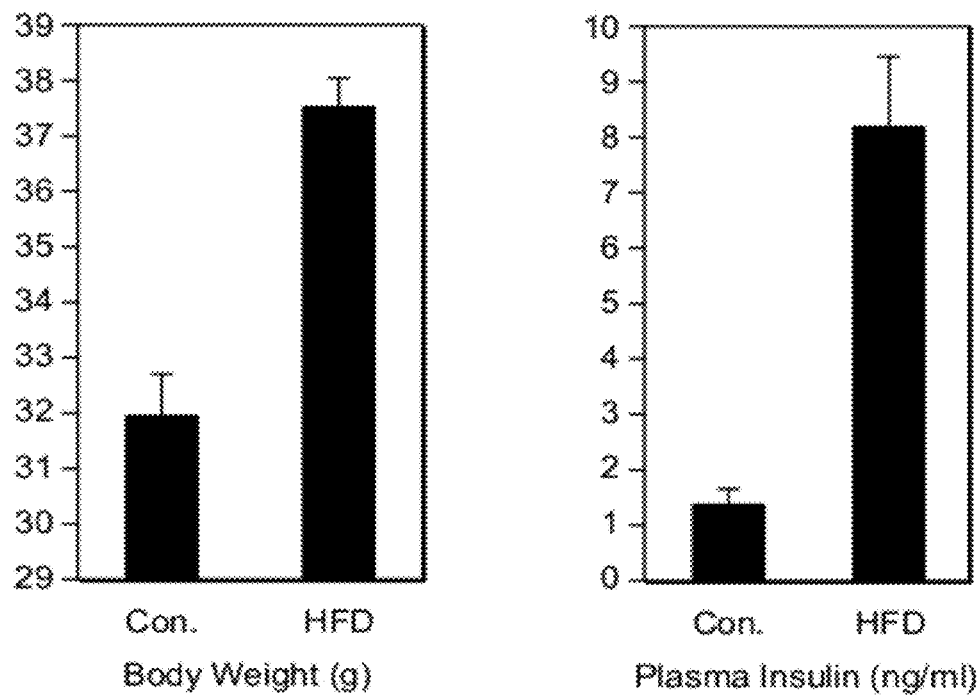
FIG. 15A shows a comparison of body weight in grams (left panel) and plasma insulin in ng/ml (right panel) in mice on a chow diet (right bars) and mice on a high fat diet (left bars).
Figure 15B:
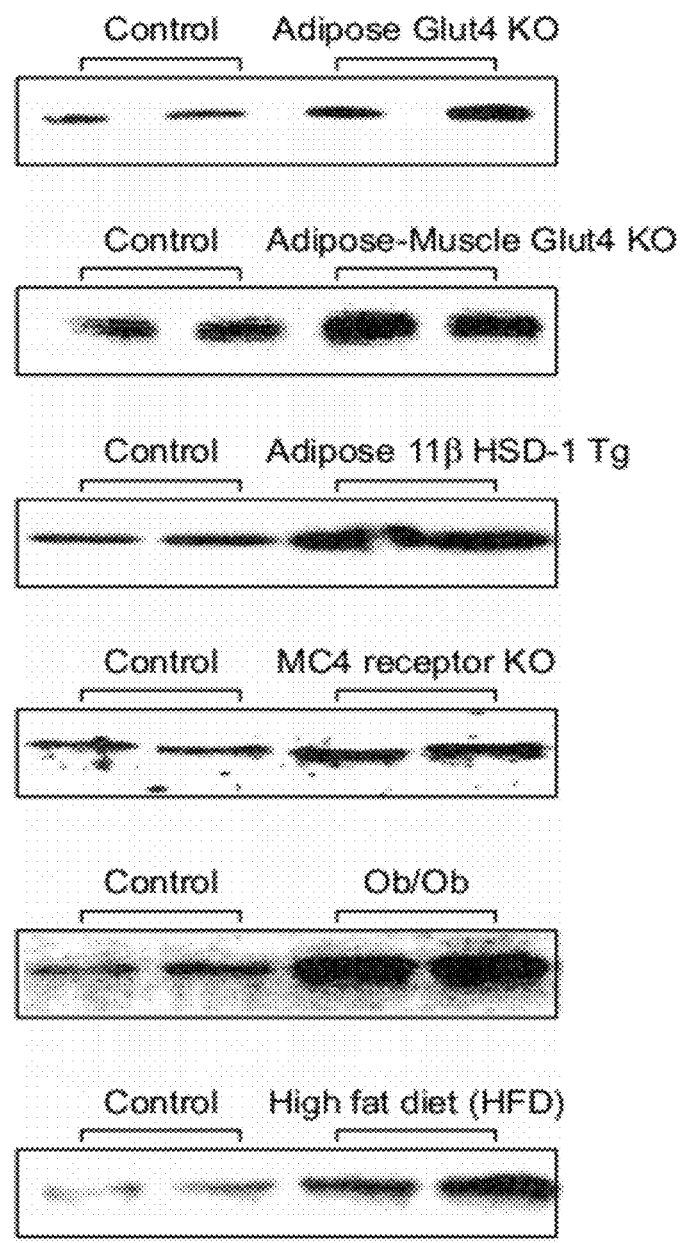
FIG. 15B shows an immunoblot of serum levels of RBP4 protein in insulin resistant mouse models; AG4KO mice (top panel), adipose-muscle GLUT4 knockout mice (second panel), adipose 11β HSD-1 overexpressor mice (third panel), MC4 receptor knockout mice (fourth panel), ob/ob mice (fifth panel), and control mice fed chow diet or a high fat diet (bottom panel).

RBP4 was identified as inversely regulated in AG4KO mice compared to control mice (CRE and FVB) and mice that overexpress GLUT4 in adipose tissue (FIG. 13). The upregulation of RBP4 mRNA was confirmed by RT-PCR (FIG. 12). As shown in FIG. 13, WAT from AG4KO mice showed over a 2-fold increase in RBP4 mRNA levels compared to wild type (FVB) WAT. As shown in FIG. 13, RBP4 mRNA is increased in AG4KO mice and decreased in adipose from mice over expressing GLUT4 (G4A$^+$). Consistent with the changes in mRNA levels in adipose tissue, serum RBP4 in AG4KO mice was elevated 2-5-fold compared to control (FVB) mice (FIG. 15B, top panel). Interestingly, RBP4 mRNA is unchanged in liver from AG4KO mice compared to mice wild-type for GLUT4 (CRE) (FIG. 14).

Serum RBP4 is increased in normal mice on a high fat diet. As shown in FIG. 15B (bottom panel), FVB mice fed a high fat diet had an increased level of serum RBP4 compared to FVB mice fed a regular chow diet. In addition, as shown in FIG. 15A, the increase in RBP4 level correlated with an increase in body weight (left panel) and an increase in plasma insulin (right panel).

Serum or plasma RBP4 was measured by diluting the serum or plasma 20 times in a standard detergent-containing buffer, separated by 15% SDS-PAGE, and transferred to nitrocellulose (Kim, Y. B., et al. *Diabetes* 48:310-320 (1999)). Mouse RBP4 and human RBP4 were detected using anti-rat or anti-human (DAKO, Germany) polyclonal antisera, respectively, followed by standard ECL detection.

III. RBP4 is a Marker for Insulin Resistance and a Drug Target for Treating Insulin Resistance

A. Serum RBP4 is Elevated in a Number of Mouse Insulin Resistance Models

As shown in FIG. 15B, serum RBP4 levels are increased in mouse models of insulin resistance including: adipose-muscle GLUT4 knockout (2-fold), adipose 11β HSD-1 over-expressers (a mouse prototype for Metabolic Syndrome; 3-fold), ob/ob mice (13-fold), MC4 receptor knockout mice (3.5-fold), and mice on a high fat diet (55% fat)(2.8-fold). The fact that elevated serum RBP4 is a general feature of insulin resistance states of diverse genetic or nutritional etiology raises the possibility that RBP4 contributes to insulin resistance.

B. Drugs that Alleviate Insulin Resistance Reverse the Increase in RBP4

Figure 18:
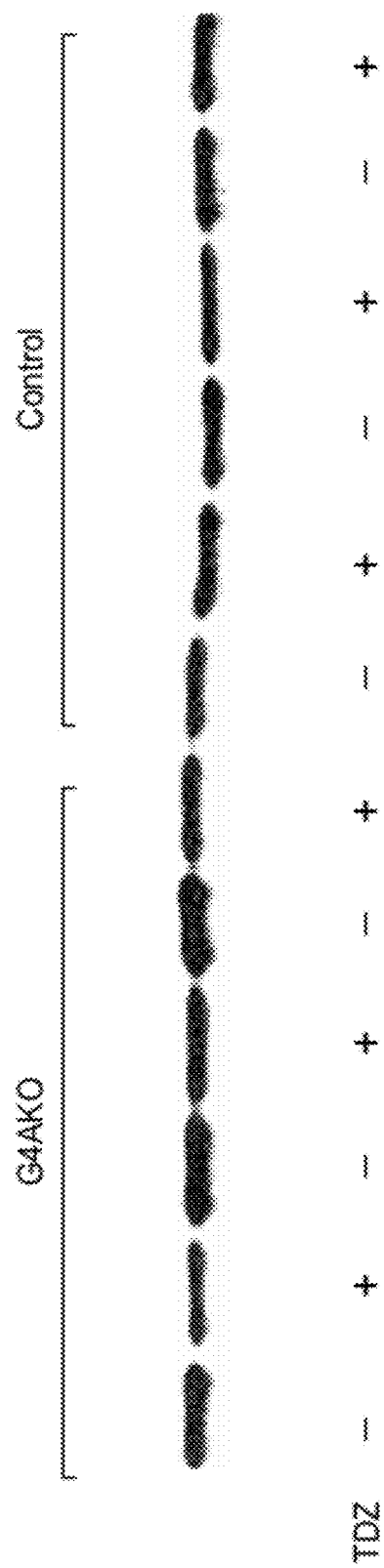
FIG. 18 shows an immunoblot of serum RBP4 from AG4KO mice (left lanes) compared to control mice (right lanes) in the presence or absence of TZD treatment.

Thiazolidinediones (TZD) are insulin sensitizing drugs that improve glucose homeostasis in AG4KO mice. As shown in FIG. 18, blood glucose and insulin were measured in both AG4KO and control mice in the absence and at the indicated time after injection with a TZD class of drug. The * in FIG. 18 indicates a P value of less than 0.05 versus control before and after treatment. The # indicates a P value of <0.05 versus GA4$^{-/-}$ mice after treatment, and "à" is a P value of <0.05 versus control before treatment. TZD treatment significantly lowered the level of blood glucose in AG4KO mice and also significantly lowered plasma insulin level in these mice. Surprisingly, treatment of AG4KO mice with a TZD class of drug decreased serum RBP4 (FIG. 21).

Treatment of AG4KO mice with an insulin-sensitizing drug for three weeks completely reversed their insulin resistance and glucose intolerance. Treatment also reduced the elevation of RBP4 mRNA in adipose tissue of AG4KO mice (FIG. 25A); RBP4 expression was not changed in the liver (FIG. 25B). mRNA levels were measured by TaqMan® real time PCR. Treatment also completely normalized the elevated serum RBP4 levels in AG4KO mice (FIGS. 25C and 25D). The dramatic effect of this insulin-sensitizing antidiabetic agent on serum RBP4 levels raises the possibility that elevation of RBP4 could play a causative role in insulin resistance and type 2 diabetes.

Plasma glucose was measured by glucometer (One Touch Ultra, Lifescan). Insulin (crystal chemical), FFAs (Wako) and adipokines (leptin, adiponectin, and resistin) (LINCO research) were measured using commercially available kits. ITT was performed by i.p. injection of recombinant regular human insulin 3-4 hours after food removal. Different insulin doses were used for different mouse lines and ages as described. GTT was performed by i.p. injection of glucose (1 or 2 g D-glucose per kg body weight) after overnight fasting.

C. Elevated Serum RBP4 Causes Insulin Resistance and Decreased Serum RBP4 Improves Insulin Action Transgenic Mice Transgenic mice expressing human RBP4 driven by the mouse muscle creatine kinase (MCK) promoter secrete RBP4 into the blood so that total serum RBP4 is approximately 2-3-fold increased, compared to non-transgenic mice. RBP4 transgenic mice developed normally and growth curves were similar to wild-type mice at least until 16 weeks of age. Serum insulin levels were higher in transgenic mice (FIG. 21). There was no difference in fed glucose, FSA, leptin, adiponectin, or resistin (FIG. 21). RBP4 over expressing mice developed mild insulin resistance by 11 weeks of age (FIG. 22A).

RBP4 Injection

To circumvent any possibility of developmental or compensatory effects of RBP4 over-expression from the beginning of embryonic development in transgenic mice, purified recombinant human RBP4 (hRBP4) was injected into normal, adult FVB mice. RBP4 is a 21 kDa protein which is easily filtered through the renal glomerular membrane. In circulation RBP4 combines transthyratin (TTR) to form an 80 kDa protein complex that prevents renal clearance of RBP4. To determine the pharmacodynamics of exogenous RBP4, 0.5 mg of recombinant hRBP4 was injected i.p. and serum hRBP4 was measured using an anti-human RBP4 antibody that has a much lower affinity for mouse RBP4 (FIG. 22B). hRBP4 could be detected 10 minutes after injection and levels peaked at 120 minutes. At 240 minutes, the level was 25% of the peak level, indicating rapid clearance. Injected RBP4 totally disappeared from the serum by 16 hours (overnight) after injection (FIG. 22B).

Human RBP4 was expressed in *E. coli* and purified according to the method described (Wang, T. T., et al. *Gene* 133: 291-294 (1993); Xie, Y. et al. *Protein Expr. Pur* 14:31-37 (1998)). Recombinant RBP4 protein was completely pure, based on staining of fluorescent staining of SDS-PAGE with SPYRO ruby (BioRad). The recombinant RBP4 protein bound retinol stoiciometrically and interacted normally with purified transthyretin. Endotoxin was removed by sequential affinity adsorption to EndoTrap matrix (ProfosAG, Germany) and Detoxi-Gel (Pierce). Purified RBP4 protein was dialyzed in a buffer containing 10 mM Hepes, 100 mM NaCl and stored frozen in stock concentrations of 7-8 mg/ml. The dialysate solution not containing RBP4 was saved for use as a vehicle controlled solution for in vivo experiments.

Endogenous mouse RBP4 concentration is about 30-40 μg/ml. To determine whether elevation of RBP4 causes insulin resistance in normal mice, 300 μg/day/mouse of purified hRBP4 divided into three doses (3-4 μg/g body weight) were injected at 8-10 hour intervals. This resulted in a daily averaged serum level of hRBP4 that is about three times higher than endogenous mouse RBP4. Control mice were injected with the same volume of dialysate solution that was obtained during the final step of RBP4 purification. RBP4 injection for 9-12 days caused insulin resistance (FIG. 22C) and glucose intolerance (FIG. 22D).

RBP4 Knockout

Figure 19:
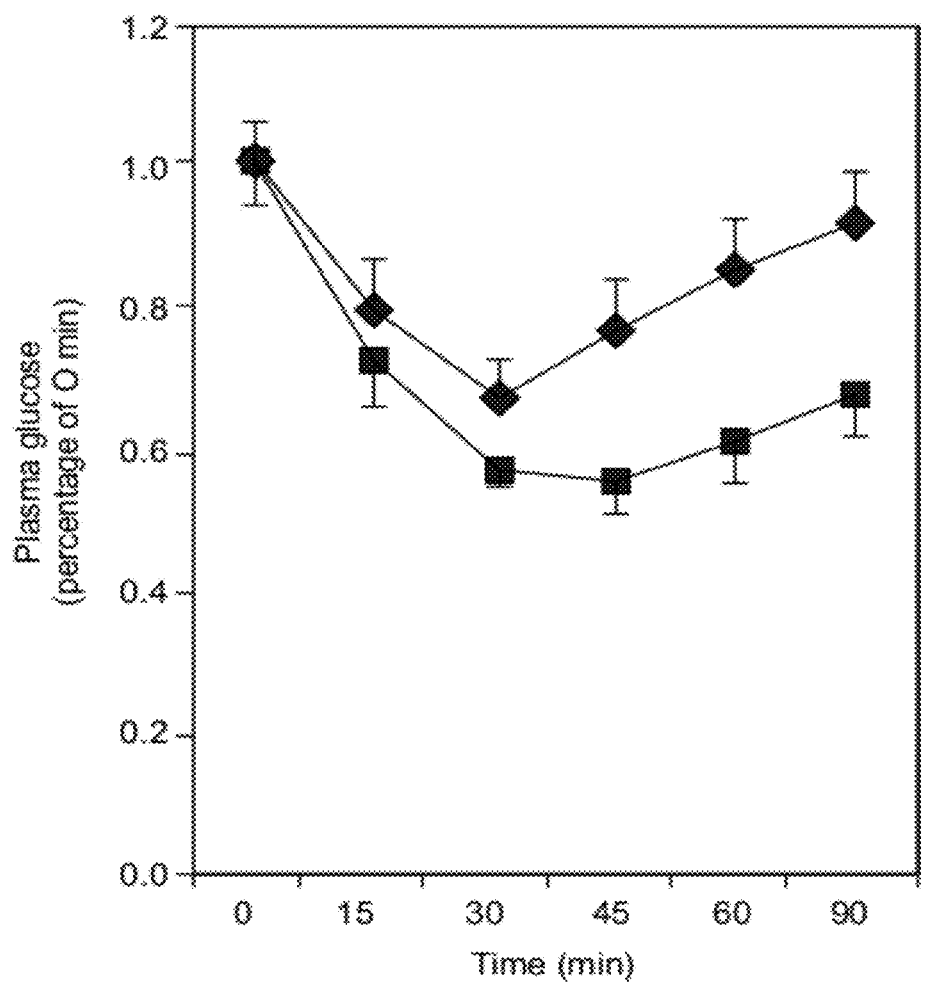
FIG. 19 shows plasma glucose (percentage at time 0) versus time after injection with insulin (0.75 U/kg body weight) in RBP4 knockout mice (squares) and control mice (diamonds).

RBP4 knockout mice (RBP4 KO) are viable and fertile with normal body weight when maintained on a vitamin A-sufficient diet (FIG. 21), but have reduced retinol levels and impaired visual function early in life. Food intake was normal. RBP4 knockout mice had improved insulin sensitivity compared to wild type mice (FIG. 19). Serum free fatty acid levels were lower in both RBP4 heteryozygous (Het) and homozygous (KO) knockout mice relative to controls (FIG. 21). Fed insulin, glucose, leptin, adiponectin and resistin were normal (FIG. 21). Both RBP4 Het and RBP4 KO mice displayed enhanced insulin sensitivity (FIG. 23A).

Fenretinide Treatment

To determine the effect of RBP4 independently of transgenic manipulation, adult FVB mice were treated with fenretinide (4-hydroxyphenyl retinamide, 4-HPR), a synthetic retinoid originally designed for cancer therapy. The bulky side chain (hydroxyphenyl group) disrupts the interaction of RBP4 with TTR, causing renal excretion of RBP4 resulting in lower serum RBP4 levels (Malpeli et al., *Biochem Biophys Acta* 1294:48-54 (1996)). Three-week old male FVB mice received chow diet, high fat diet or high fat diet supplemented with 0.04% fenretinide. Fenretinide gel capsules were emptied and added directly to the fat soluble vitamin component of the Harlan-Teklad laboratory high fat diet in at the time of diet preparation. Light exposure was minimized during fenretinide high fat diet preparation. Fenretinide high fat diet was stored in the dark at 4° C. and were placed in mouse cages at 2-3 day intervals. Oral administration of fenretinide lowered serum RBP4 levels in obese mice on a high fat diet (HFD) to the level of non-obese control mice on a chow diet (FIGS. 23B and 23C). Fenretinide treatment did not affect food intake, body weight, or the development of obesity on the high fat diet. HFD mice developed marked insulin resistance (FIG. 23D) and glucose intolerance (FIG. 23E). Fenretinide treatment improved insulin sensitivity (FIG. 23D) and normalized glucose tolerance (FIG. 23E). Thus, both genetic and pharmacological interventions that decrease RBP4 levels improve insulin sensitivity even in obesity.

Fenretinide Treatment of ob/ob Mice

Fenretinide Treatment Improves Glucose Tolerance of ob/ob Mice.

IPGTT (2 mg/g body weight) was performed on mice (12 weeks old) after 8 weeks of diet/treatment (FIG. 26A). Plasma glucose was measured at the indicated times; the open circles represent ob/+, the closed circles represent ob/ob mice and the open squares represent ob/ob mice treated with fenretinide. As show in FIG. 26A, treatment of ob/ob mice with fenretinide greatly improved their glucose tolerance.

Fenretinide Treatment Causes a Sustained Improvement in Glucose Tolerance of ob/ob Mice IPGTT (1 mg/g body weight) was performed on mice (42 weeks old). After 38 weeks of diet/treatment (FIG. 26B), plasma glucose was measured at the indicated times; the closed squares are ob/+, the closed circles are ob/+ mice treated with fenretinide; open squares are ob/ob and open circles are ob/ob treated with fenretinide. As shown in FIG. 26B, after 38 weeks of treatment with fenretinide improve glucosed disposal to nearly that of heterozygous mice.

Fenretinide Treatment Reduces Long-Term Mortality of ob/ob Mice.

After 10 months of treatment with fenretinide, long term mortality of ob/ob mice (closed circles) was reduced by almost half compared to untreated controls (open circles) and ob/+ heterozygous mice (closed squares). The ob/ob mice at 10 months of age were severely obese.

D. RBP4 Alters PI3 Kinase (PI3K) Activity in Muscles

To understand how RBP4 alters insulin sensitivity, insulin signal transduction in muscle and liver of RBP4 Tg and KO mice was studied.

Mice were fasted for 16-18 hours, injected i.v. with saline or insulin (10 U per kg body weight) and killed three minutes after injection. Tissues were collected and frozen. PI3K activity was measured in phosphotyrosine immunoprecipitates from muscle and liver lysates as described (Kim, Y. B., et al, *Diabetes* 48:311-320 (1999)).

The basal level of PI3K activity was similar in all genotypes (FIGS. 24A-24D). Insulin-stimulated PI3K activity 26-fold in muscle of control mice, but the effect was reduced by 30% in RBP4 Tg mice (FIG. 24A). Conversely, insulin-stimulated PI3K activity was increased by 80% in muscle of both RBP4 Het and RBP4 KO mice compared to controls (FIG. 24B). However, PI3K activity was not altered in the liver of RBP4 Tg (FIG. 24C) or RBP4 KO mice (FIG. 24D). Consistent with these observations, RBP4 injection for 21 days in wild-type mice caused a 34% reduction in insulin-stimulated PI3K activity in muscle, but no alteration in liver (FIG. 24E). Furthermore, RBP4 treatment resulted in a 24% reduction in insulin-stimulated tyrosine phosphorylation of insulin receptor substrate-1 (IRS1) at residue 612 (FIG. 24F), an important site for docking of the p85 subunit of PI3K. However, RBP4 treatment did not alter insulin receptor (IR) tyrosine phosphorylation (FIG. 24G) or the total amount of IRF1 or IR proteins. These data suggest that RBP4 alters insulin sensitivity by affecting insulin signaling in muscle at the steps of IRF1 phosphorylation and PI3K activation. Similar post-receptor defects were observed in the muscle of AG4KO mice, consistent with the proposition that elevated serum RBP4 contributes to systemic insulin resistance in this model of type 2 diabetes.

IV. Human Data Agrees

Figure 20B:
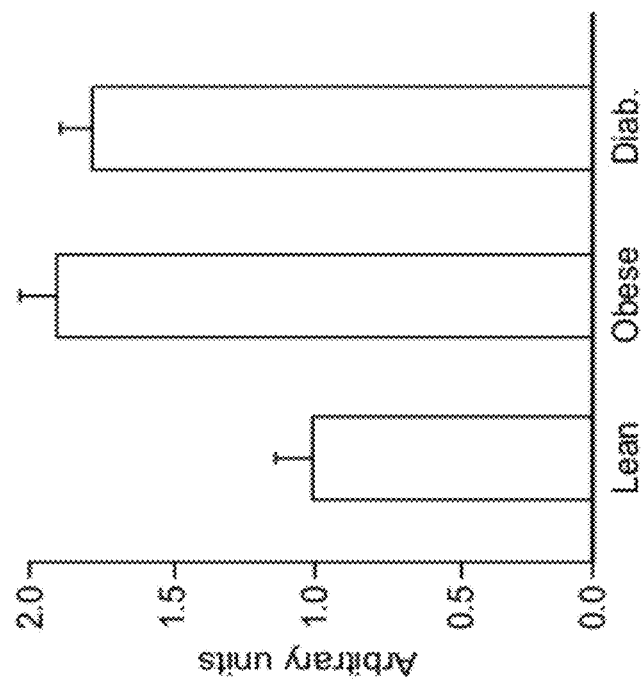
FIG. 20B shows a quantitative analysis of the results from FIG. 20A in arbitrary units.
Figure 20A:
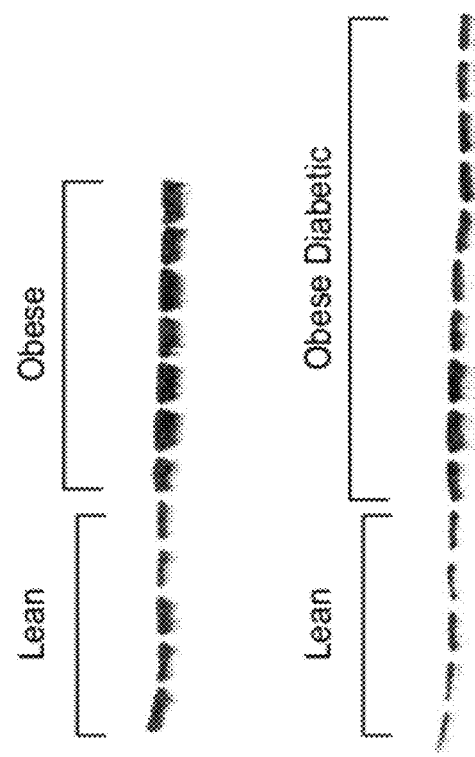
FIG. 20A shows immunoblots of serum RBP4 from lean non-diabetic humans (left lanes), obese non-diabetic humans (top panel, right lanes), and obese diabetic humans (bottom panel, right lanes).

Serum RBP4 is elevated in obese and obese/diabetic humans but not lean, non-diabetic humans. Obese-diabetic subjects were older than obese non-diabetic and lean non-diabetic control subjects (FIG. 20). Obese and obese-diabetic subjects had higher BMI and fasting insulin levels and lower GDR, measured by euglycemic-hyperinsulinemic clamp studies, as compared to lean non-diabetic subjects. FIG. 20A shows an immunoblot of serum from obese and obese/diabetic humans. As shown in FIG. 20A, obese and obese/diabetic humans have an increased level of RBP4. FIG. 20B demonstrates that this level is nearly two-fold increased. There was no difference in the magnitude of serum RBP4 elevation between the obese and obese-diabetic groups, suggesting that obesity and insulin resistance, but no hyperglycemia, are associated with elevated serum RBP4 in humans.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying a compound that reduces circulating levels of RBP4 in the blood or tissue of a mammal comprising the steps of:
   a) administering a test compound to a mammal, wherein the mammal is a mouse that has been genetically or nutritionally engineered to exhibit insulin resistance;
   b) obtaining a biological sample from the mammal and performing an assay to determine the level of RBP4 protein, or characteristic fragment thereof, or RBP4 mRNA in the sample, and;
   c) comparing the level of RBP4 protein, or characteristic fragment thereof, or RBP4 mRNA in the sample after administration of the test compound to the level of RBP4 protein, or characteristic fragment thereof, or RBP4 mRNA in a control sample prior to administration of the test compound, wherein a decrease in RBP4 protein, or a characteristic fragment thereof, or RBP4 mRNA in the sample after administration of the test compound as compared to the control sample indicates that the compound reduces levels of RBP4 in the tissue or blood.

2. The method of claim 1 wherein the biological sample is selected from the group consisting of liver tissue, adipose tissue, whole blood, serum and plasma.

3. The method of claim 1 wherein the mouse is selected from the group consisting of: an AG4KO; mouse; an adipose-muscle GLUT4 knockout; mouse; an adipose 11B HSD-1 over-expressor mouse; an ob/ob mouse; a MC4 receptor knockout mouse, or a RBP4 over-expressor mouse.

4. The method of claim 1 wherein the assay is an immunoassay comprising an anti-RBP4 antibody.

5. The method of claim 4 wherein the immunoassay is an ELISA, an RIA, a nephlometry assay, or a Western blot assay.

6. The method of claim 4 wherein the biological sample or antibody is immobilized on a solid support.

7. The method of claim 6 wherein the solid support is filter paper.

8. The method of claim 1 wherein the assay comprises a Northern blot assay, real-time PCR, RT-PCR or RNase protection assay.

9. A method of identifying a compound that reduces circulating levels of RBP4 in the blood of a mammal comprising the steps of:
   a) administering a test compound to a mammal, wherein the mammal is a mouse that has been genetically or nutritionally engineered to exhibit insulin resistance;
   b) obtaining a urine sample from the mammal and performing an assay to determine the level of RBP4 protein, or characteristic fragment thereof, in the urine sample, and;
   c) comparing the level of RBP4 protein, or characteristic fragment thereof, in the urine sample after administration of the test compound to the level of RBP4 protein, or characteristic fragment thereof, in a control urine sample prior to administration of the test compound, wherein an increase in RBP4 protein, or a characteristic fragment in the urine sample after administration of the test compound as compared to the control sample indicates that the compound reduces circulating levels of RBP4 in the blood.

10. The method of claim 9 wherein the mouse is selected from the group consisting of: an AG4KO; mouse; an adipose-muscle GLUT4 knockout; mouse; an adipose 11B HSD-1 over-expressor mouse; an ob/ob mouse; a MC4 receptor knockout mouse, or a RBP4 over-expressor mouse.

11. The method of claim 9 wherein the assay is an immunoassay comprising an anti-RBP4 antibody.

12. The method of claim 11 wherein the immunoassay is an ELISA, an RIA, a nephlometry assay, or a Western blot assay.

13. The method of claim 11 wherein the biological sample or antibody is immobilized on a solid support.

14. The method of claim 13 wherein the solid support is filter paper.

* * * * *

UNITED STATES PATENT AND TRADEMARK OFFICE
CERTIFICATE OF CORRECTION

PATENT NO. : 8,568,969 B2  Page 1 of 1
APPLICATION NO. : 13/477790
DATED : October 29, 2013
INVENTOR(S) : Barbara B. Kahn et al.

It is certified that error appears in the above-identified patent and that said Letters Patent is hereby corrected as shown below:

In the Claims:
In Column 25, lines 20 and 21, Claim 1, delete "circulating"

Signed and Sealed this
Fourth Day of February, 2014

Michelle K. Lee
*Deputy Director of the United States Patent and Trademark Office*